US012187737B2

(12) United States Patent
Mekonnen et al.

(10) Patent No.: US 12,187,737 B2
(45) Date of Patent: Jan. 7, 2025

(54) IMIDAZOLO DERIVATIVES, COMPOSITIONS AND METHODS AS OREXIN ANTAGONISTS

(71) Applicant: HAGER BIOSCIENCES, LLC, Bethlehem, PA (US)

(72) Inventors: Belew Mekonnen, Bethlehem, PA (US); Hemantbhai Patel, Bethlehem, PA (US)

(73) Assignee: Hager Biosciences, LLC, Bethlehem, PA (US)

( * ) Notice: Subject to any disclaimer, the term of this patent is extended or adjusted under 35 U.S.C. 154(b) by 671 days.

(21) Appl. No.: 17/616,152

(22) PCT Filed: Jun. 3, 2020

(86) PCT No.: PCT/US2020/035848
§ 371 (c)(1),
(2) Date: Dec. 2, 2021

(87) PCT Pub. No.: WO2020/247445
PCT Pub. Date: Dec. 10, 2020

(65) Prior Publication Data
US 2022/0259224 A1    Aug. 18, 2022

Related U.S. Application Data

(60) Provisional application No. 62/856,830, filed on Jun. 4, 2019.

(51) Int. Cl.
*C07D 498/04* (2006.01)
*C07D 513/04* (2006.01)

(52) U.S. Cl.
CPC ......... *C07D 498/04* (2013.01); *C07D 513/04* (2013.01)

(58) Field of Classification Search
CPC ........................... C07D 498/04; C07D 513/04
USPC ....................................................... 514/275
See application file for complete search history.

(56) References Cited

U.S. PATENT DOCUMENTS

| | | | |
|---|---|---|---|
| 4,977,161 A | 12/1990 | Fujikawa et al. |
| 5,547,978 A | 8/1996 | Christensen et al. |
| 6,326,382 B1 | 12/2001 | Villalobos et al. |
| 6,372,757 B1 | 4/2002 | Johns et al. |
| 6,677,354 B2 | 1/2004 | Branch et al. |
| 6,943,160 B2 | 9/2005 | Branch et al. |
| 7,432,270 B2 | 10/2008 | Branch et al. |
| 8,569,311 B2 | 10/2013 | Breslin et al. |
| 8,710,076 B2 | 4/2014 | Branch et al. |
| 8,669,272 B2 | 11/2014 | Breslin et al. |
| 8,916,584 B2 | 12/2014 | Conn et al. |
| 9,499,517 B2 | 11/2016 | Kamenecka et al. |
| 2006/0040937 A1 | 2/2006 | Branch et al. |
| 2006/0135447 A1 | 6/2006 | Chupak et al. |
| 2007/0265249 A1 | 11/2007 | Cowart et al. |
| 2008/0119515 A1 | 5/2008 | Siddiqui et al. |
| 2008/0132490 A1 | 6/2008 | Bergman et al. |
| 2008/0300256 A1 | 12/2008 | Frank et al. |
| 2009/0012073 A1 | 1/2009 | Branch et al. |
| 2009/0082390 A1 | 3/2009 | Chan et al. |
| 2009/0118200 A1 | 5/2009 | Bergman et al. |
| 2009/0203736 A1 | 8/2009 | Knust et al. |
| 2010/0168134 A1 | 7/2010 | Breslin et al. |
| 2010/0184808 A1 | 7/2010 | Aissaoui et al. |
| 2010/0317688 A1 | 12/2010 | Peyronel |
| 2011/0003835 A1 | 1/2011 | Mueller et al. |
| 2011/0263643 A1 | 10/2011 | Cox et al. |
| 2012/0065205 A1 | 3/2012 | Mercer et al. |
| 2012/0101106 A1 | 4/2012 | Mercer et al. |
| 2012/0165339 A1 | 6/2012 | Terauchi et al. |
| 2012/0295921 A1 | 11/2012 | Breslin et al. |
| 2013/0217727 A1 | 8/2013 | Benting et al. |
| 2014/0228377 A1 | 8/2014 | Abe et al. |
| 2014/0275065 A1 | 9/2014 | Coate et al. |
| 2014/0364432 A1 | 12/2014 | Kamenecka et al. |
| 2015/0038502 A1 | 2/2015 | Li et al. |
| 2018/0222896 A1 | 8/2018 | Kaieda et al. |
| 2022/0315602 A1 | 10/2022 | Mekonnen et al. |

FOREIGN PATENT DOCUMENTS

| | | |
|---|---|---|
| EP | 2730573 A1 | 5/2014 |
| WO | 1999/058533 | 11/1999 |
| WO | 2000/037458 | 6/2000 |
| WO | 2001/096302 | 12/2001 |

(Continued)

OTHER PUBLICATIONS

Aboul-Fadl, et al. Effective and Variable Functionalization of Pyrazolo[1,5-a]pyridines Involving Palladium-Catalyzed Coupling Reactions. Synthesis, No. 12, pp. 1727-1732 (2000).

Heifetz, et al. Toward an Understanding of Agonist Binding to Human Orexin-1 and Orexin-2 Receptos with G-Protein-Coupled Receptor Modeling and Site-Directed Mutagenesis. Biochemistry 2013, 52, 8246-8260.

Heifetz, et al. Discovery of the First Selective, Nonpeptidic Orexin 2 Receptor Agonists. J. Med. Chem. 2015, 58, 7928-7930.

Heifetz, et al. Using the fragment molecular orbital method to investigate agonist-orexin-2 receptor interactions. Biochem. Soc. Trans. 2016, 44, 574-581.

Yin, et al. Crystal Structure of the human OX2 orexin receptor bound to the insomnia drug suvorexant. Nature, 519: 247-250 (2015).

(Continued)

*Primary Examiner* — Kahsay Habte
(74) *Attorney, Agent, or Firm* — Patrick J. Halloran

(57) ABSTRACT

This disclosure is directed to substituted Imidazolo[2,1-b]oxazole, Imidazolo[2,1-b]thiazole, Imidazolo[2,1-b]oxadiazole, Imidazolo[2,1-b]oxadiathiazole derivatives of compounds that are antagonists of orexin receptors, and which are useful in the treatment or prevention of neurological and psychiatric disorders and diseases in which orexin receptors are involved or implicated. The invention is also directed to pharmaceutical compositions comprising these compounds and the use of these compounds and compositions in the prevention or treatment of such diseases in which orexin receptors are involved.

16 Claims, No Drawings

(56) References Cited

FOREIGN PATENT DOCUMENTS

| WO | 2002/044172 | 6/2002 |
|----|----|----|
| WO | 2002/090355 | 11/2002 |
| WO | 2003/051873 | 6/2003 |
| WO | 2003051873 A2 | 6/2003 |
| WO | 2004026866 A1 | 4/2004 |
| WO | 2006/127550 | 11/2006 |
| WO | 2008/147518 | 12/2008 |
| WO | 2010/048010 | 4/2010 |
| WO | 2010/048012 | 4/2010 |
| WO | 2010/141275 | 12/2010 |
| WO | 2011/005636 | 1/2011 |
| WO | 2011/100614 | 8/2011 |
| WO | 2013062858 A1 | 5/2013 |
| WO | 2020/247447 | 12/2020 |
| WO | 03002559 A2 | 6/2022 |

OTHER PUBLICATIONS

PubChem-SID-384300382, Modify Date: May 31, 2019 (May 31, 2019) <https://pubchem.ncbi.nlm.nih.gov/substance/384300382>.

PubChem-SID-404587974, Modify Date: Feb. 27, 2020 (Feb. 27, 2020) <https://pubchem.ncbi.nlm.nih.gov/substance/404587974>.

PubChemCompound Record for CID 60368629 Date Oct. 18, 2012 (Oct. 18, 2012) <https://pubchem.ncbi.nlm.nih.gov/compound/60368629>.

International Search Report for EP 2730573 dated Sep. 18, 2012.

Supplementary European Search Report for EP 2771346 dated Apr. 23, 2015.

Volochnyuk et al. "Approach to the library of fused pyridine-4-carboxylic acids by Combes-type reaction of acyl pyruvates and electron-rich amino heterocycles." Journal of Combinatorial Chemistry 12.4 (2010): 510-517.

International Search Report for PCT/JP2012/067038 dated Sep. 18, 2012.

International Search Report for PCT/US2012/060927 dated Jan. 30, 2013.

International Search Report for PCT/EP2002/007007 dated Mar. 27, 2003.

International Search Report for PCT/EP2003/010412 dated Jan. 22, 2004.

International Search Report and Written Opinion for PCT/US2020/035848 dated Aug. 27, 2020.

European Search Report for EP 20818543 dated May 3, 2023.

International Search Report and Written Opinion for PCT/US2020/035851 dated Aug. 19, 2020.

European Search Report for EP 20817900 dated Dec. 16, 2022.

Cox, et al. Discovery of the Dual Orexin Receptor Antagonist [(7R)-4-(5-Chloro-1,3-benzoxazol-2-yl)-7-methyl-1,4-diazepan-1-yl][5-methyl-2-(2H-1,2,3-triazol-2-yl)phenyl]methanone (MK-4305) for the Treatment of Insomnia. J. Med. Chem. 2010, 53, 5320-5332.

Heifitz, et al. Study of Human Orexin-1 and-2 G-Protein-Coupled Receptors with Novel and Published Antagonists by Modeling, Molecular Dynamics Simulations, and Site-Directed Mutagenesis. Biochemistry 2012, 51, 3178-3197.

Cox, et al. Discovery of the dual orexin receptor antagonist [(7R)-4-(5-chloro-1,3-benzoxalzol-2-yl)-7-methyl-1,4-diazepan-1-yl][5-methyl-2-(2H-1,2,3-triazol-2-yl)phenyl)methanone (MK-4305) for the treatment of insomnia. J. Med. Chem., 53(14), 5320-32 (2010).

Marshall et al. Absolute configuration of .alpha.-methyldopamine formed metabolically from .alpha.-methyldopa in man. Journal of Medicinal Chemistry 16 (3), 266-270 (1973).

Morris, et al. Dual Antagonists of the Human Orexin 1 and 2 Receptors.

Yin, et al. Structure and ligand-binding mechanism of the human OX1 and OX2 orexin receptors. Nature Structural & Molecular Biology, 23(4): 293-299 (2016).

IMIDAZOLO DERIVATIVES, COMPOSITIONS AND METHODS AS OREXIN ANTAGONISTS

RELATED APPLICATIONS

This application claims priority to U.S. Provisional Application Ser. No. 62/856,830 filed on Jun. 4, 2019, the contents are which are hereby incorporated into this application in its entirety.

FIELD OF THE DISCLOSURE

This disclosure pertains to compounds, compositions and methods for using orexin antagonists to treat or ameliorate human and animal diseases as therapeutic agents. In particular, any pathological disorder in which both types of orexin receptors are pharmacologically involved or implicated. These important therapeutic applications include but are not limited to treating central nervous system (CNS) disorders and neurological diseases that involve or are modulated by orexin receptors including but not limited to disorders that are responsive to orexin receptor antagonists, e.g., substance addiction and dependence, cognitive impairment, Alzheimer's disease (AD), posttraumatic stress disorder (PTSD), schizophrenia, panic, anxiety, autism, and depression.

BACKGROUND INFORMATION

The orexins (also known as hypocretins) are comprised of two excitatory hypothalamic neuropeptides: orexin A (OX-A; a 33 amino acid peptide) and orexin B (OX-B; a 28 amino acid peptide). They were simultaneously discovered in 1998 by two research groups searching for new signaling molecules, (1) Sakurai and co-workers (who named them orexin-A and -B) (Sakurai, T. et al, *Cell* 1998, 92, 573) and (2) de Lecea and co-workers (who named them hypocretin 1 and 2, respectively) (de Lecea, L. et al, *Proc. Natl. Acad. Sci. U.S.A.* 1998, 95, 322.). These neuropeptides are endogenous ligands for two G protein-coupled receptors (GPCR) named $OX_1R$ and $OX_2R$ (also referred to as Hcrt1 and Hcrt2, respectively) and are derived proteolytically from the same precursor peptide called pre-pro-orexin polypeptide (Sakurai T., et al. *The Journal of biological chemistry.* 1999; 274, 17771-17776). Though structurally related, the binding affinities of these endogenous ligands for the two GPCRs differ. Orexin A binds to $OX_1R$ with about 100-fold higher affinity than Orexin B, whilst both Orexin A and Orexin B bind to OX2R with the same affinity (Kodadek, T.; Cai, D. *Mol. BioSyst.,* 2010, 6, 1366-1375). Soon after the discovery of orexins, modulation of the orexin signaling was originally considered for potential novel treatments of narcoleptic or insomniac patients since the role of orexins in regulation of sleep and wakefulness was well-studied and understood, and the discovery of small-molecule modulators of orexin signaling facilitated the development of this class of compounds. Narcoleptic patients show a diminished activity in hypothalamic orexin neurons thereby lowering the amounts of circulating orexins in the cerebrospinal fluid. In contrast, activation of orexin neurons maintains wakefulness and arousal. The effects of orexin signaling on feeding and energy homeostasis were also established earlier and found to be coordinated to the sleep-wake cycle (Kodadek, T.; Cai, D. *Mol. BioSyst.,* 2010, 6, 1366-1375). More recent studies have established the role of orexin signaling in other key physiological pathways such as neuroendocrine functions (Inutsuka, A.; Yamanaka, A. *Front. Endocrinol.* 2013, 4:18. doi: 10.3389/fendo.2013.00018), glucose metabolism (Tsuneki, H., et al., *Endocrinology,* 2016, 157, 4146-4157), stress-adaptive responses (Xiao, F., et al. *Neuropharmacology,* 2013, 67, 16-24), and addiction/reward-seeking (Aston-Jones, G., et al. *Brain Res.,* 2010, 1314, 74-90). Small molecule orexin antagonists have been broadly categorized into three classes based on their overall receptor selectivity profiles: (1) DORA (dual-acting, or non-selective $OX_1R/OX_2R$ antagonists), (2) SORA-1 (selective $OX_1R$ antagonists), and (3) SORA-2 (selective $OX_2R$ antagonists). It has been shown that while $OX_2R$ knockout mice and $OX_1R/OX_2R$ double knockout mice both show a narcoleptic phenotype, the effect is very muted in $OX_1R$ knockouts (Wang C., et al. *Neurosci.,* 2018, 11, 220. doi: 10.3389/fnmol.2018.00220). Additionally, both DORA and SORA-2 compounds inhibit wakefulness, but SORA-1 compounds do not—thus suggesting that narcoleptic effects are mediated through $OX_2R$ or a combination of $OX_1R$ and $OX_2R$, but not through $OX_1R$ alone. Thus, it is clear that the discovery and development of selective orexin antagonists is crucial to the advancement of this field but most importantly to the development of therapeutic agents for dysregulated biological processes that involve the orexin receptor; especially for non-sleep related indications such as substance addiction.

SUMMARY OF THE DISCLOSURE

This disclosure addresses the aforementioned therapeutic need by providing compounds of formula I:

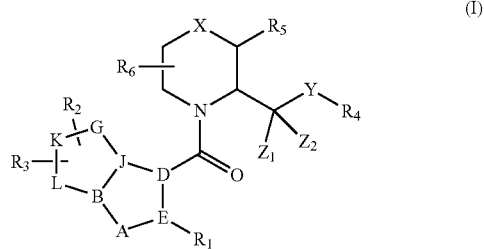

wherein the variables are as defined herein, including any pharmaceutically acceptable salts, solvates, adducts, polymorphs, and isomers thereof. Compounds of formula I can be used to treat the conditions described herein, such as through activity as orexin receptor antagonists. In some embodiments, compounds of formula I and compositions comprising the same can be used to treat conditions such as those described herein, such as through activity as Orexin receptor antagonists. Thus, the compounds and/or compositions of the same can be referred to herein as "Orexin receptor antagonists".

This disclosure also provides compositions that comprise the above compounds or a pharmaceutically acceptable salt thereof. In another aspect of the invention, there is provided a method for treating CNS disorders, among others, substance addiction and dependence, posttraumatic stress disorder (PTSD), schizophrenia, panic, anxiety and depression, cognitive impairment and Alzheimer's disease (AD) in a subject in need or at risk thereof, the method comprising the step of administering to said subject a therapeutically effective amount of Orexin receptor antagonists or a pharmaceutically acceptable salt thereof. In certain embodiments of the invention, the Orexin receptor antagonists or a pharmaceutically acceptable salt thereof could be formulated to be administered periodically, for example every 3, 6 to 24 hours as deemed clinically beneficial. Other aspects and embodiments are contemplated herein as would be understood by those of ordinary skill in the art.

DETAILED DESCRIPTION

This disclosure pertains to a fused six (6) and five (5) membered ring system derivatives of formula (I) wherein the fused 6 & 5 membered rings are as described in the full invention enabling structural descriptions, to pharmaceutically acceptable salts thereof, to their preparation, to pharmaceutical compositions containing one or more compounds of formula (I), and to their use as pharmaceuticals and therapeutic agents, particularly (i.e., in preferred embodiments) to the use of the same as orexin receptor antagonists ("Orexin receptor antagonists"). These novel agents as described by formula (I) which are non-peptide antagonists of human orexin receptors and are potentially useful in the treatment of disorders relating to orexinergic dysfunctions; including but not limited for such disorders like substance addiction, anxiety, panic, cognitive dysfunctions, mood, or appetite, sleep, Alzheimer (AD), metabolic syndrome, and hypertension; and especially these compounds could be of great therapeutic value in the treatment of anxiety disorders, addiction disorders, and sleep disorders.

In some embodiments, this disclosure provides compounds of the formula (I),

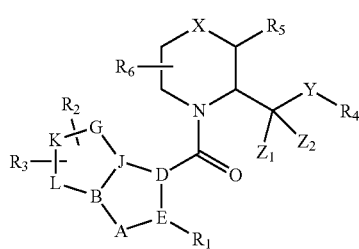

(I)

wherein:

$R_1$=aromatic or aryl, heteroaryl (5-6 membered ring), substituted aromatic or aryl, substituted heteroaryl (5-6 membered ring); when $R_1$ is heteroaryl, it is preferred as a 5- or 6-membered heteroaryl selected from the group consisting of pyrrolyl, pyrazolyl, triazolyl, oxazolyl, thiazolyl, oxadiazolyl, thiophenyl, pyridinyl, pyrimidinyl, pyrazinyl, and pyridazinyl; wherein said aromatic, aryl or heteroaryl is unsubstituted, mono-, or di-substituted, wherein the substituents are independently selected from the group consisting of $(C_{1-4})$alkyl, $(C_{1-4})$alkoxy, halogen, $(C_{1-3})$fluoroalkyl, $(C_{1-3})$fluoroalkoxy, and $(C_{3-7})$cycloalkyl; wherein the halogen is optionally selected from the group consisting of F, Cl, Br, and I;

$R_2$, $R_3$=H, halogen (such as F, Cl, Br or I), alkyl group, substituted alkyl, $(C_{1-4})$alkyl, $(C_{1-4})$alkoxy, halogen, $(C_{1-3})$fluoroalkyl, $(C_{1-3})$fluoroalkoxy, and $(C_{3-7})$cycloalkyl; wherein each of $R_2$ and $R_3$ is independently and optionally substituted at each substitutable position with up to 3 substituents independently selected from one or both $R_2$ and $R_3$; wherein the halogen is selected from the group consisting of F, Cl, Br, and I;

$R_4$=aromatic or aryl, heteroaryl (5-6 membered ring), substituted aromatic or aryl, substituted heteroaryl (5-6 membered ring); wherein said aromatic, aryl or heteroaryl is unsubstituted, mono-, or di-substituted or tri-substituted, wherein the substituents are independently selected from the group consisting of phenyl, $(C_{1-4})$alkyl, $(C_{1-4}$alkoxy, halogen, $(C_{1-3})$fluoroalkyl, $(C_{1-3})$fluoroalkoxy, and $(C_{3-7})$cycloalkyl, $(C_{3-7})$heterocycloalkyl; wherein the halogen is selected from the group consisting of F, Cl, Br, and I;

$R_5$=$CH_3$, alkyl group, or substituted alkyl; wherein $R_5$ and $R_6$ can be connected as alkyl group to form a $(C_{1-3})$ alkyl bridge cyclic structure;

$R_6$=H, halogen (F, Cl, Br, or I), alkyl group, or substituted alkyl; wherein $R_5$ and $R_6$ can be connected as alkyl group to form a $(C_{1-3})$alkyl bridge cyclic structure;

X=$CH_2$, O, or nothing (to provide five membered pyrrolidine ring); wherein the carbon atom at position 2 of the piperidine or pyrrolidine is preferred in absolute (S)-configuration; in contrast, the carbon atom at position 2 of the morpholine ring (when X=O, oxygen) is preferred in absolute (R)-configuration;

Y=NH, O, nothing (to attach $R_4$ directly to $CZ_1Z_2$ group), $CH_2OR_4$, $CH_2$, or $NR_4R_7$ (where $R_7$=H, alkyl);

$Z_1$ and $Z_2$ independently=H, F, $(C_{1-4})$alkyl, $(C_{1-3})$fluoroalkyl, $(C_{1-3})$fluoroalkoxy, or $(C_{2-7})$cycloalkyl; Also wherein:

Fused ring system A-B-J-D-E: five (5)-membered heteroaryl;

Fused ring system B-J-G-K-L: five (5)-membered aromatic or aryl, heteroaryl, cycloalkyl, or heterocycloalkyl;

wherein the preferred groups are:

A=Nitrogen (N);
B=Carbon (C) or Nitrogen (N);
J=Carbon (C) or Nitrogen (N);
D=Carbon (C);
E=Carbon (C);
G=Carbon (C), Nitrogen (N), CH, $CR_2R_3$, $CR_2$, $CR_3$, or O;
K=Carbon, CH, $CR_2R_3$, $CR_2$, $CR_3$, or O; and,
L=O, S, $CR_2R_3$, $CHR_2$, or $CHR_3$;

or a pharmaceutically acceptable salt, hydrate, solvate, polymorph, isomer, or combination thereof.

In some preferred embodiments, this disclosure provides a compound that has the formula II, wherein the ring system illustrated by A-B-J-D-E variables in formula (I) fused to the 5-membered ring is preferred as an imidazolo ring system as represented by embodiment formula (II) herein:

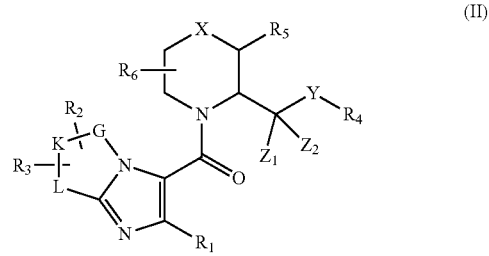

(II)

wherein:

$R_1$=aromatic or aryl, heteroaryl (5-6 membered ring), substituted aromatic or aryl, substituted heteroaryl (5-6 membered ring); when $R_1$ is heteroaryl, it is preferred as a 5- or 6-membered heteroaryl selected from the group consisting of pyrrolyl, pyrazolyl, triazolyl, oxazolyl, thiazolyl, oxadiazolyl, thiophenyl, pyridinyl, pyrimidinyl, pyrazinyl, and pyridazinyl; wherein said aromatic, aryl or heteroaryl is unsubstituted, mono-, or di-substituted, wherein the substituents are independently selected from the group consisting of $(C_{1-4})$ alkyl, $(C_{1-4})$alkoxy, halogen, $(C_{1-3})$fluoroalkyl, $(C_{1-3})$ fluoroalkoxy, and $(C_{3-7})$cycloalkyl; wherein the halogen is optionally selected from the group consisting of F, Cl, Br, and I;

$R_2$, $R_3$=H, halogen (such as F, Cl, Br or I), alkyl group, substituted alkyl, $(C_{1-4})$alkyl, $(C_{1-4})$alkoxy, halogen, $(C_{1-3})$fluoroalkyl, $(C_{1-3})$fluoroalkoxy, and $(C_{3-7})$cycloalkyl; wherein each of $R_2$ and $R_3$ is independently and optionally substituted at each substitutable position with up to 3 substituents independently selected from one or both $R_2$ and $R_3$; wherein the halogen is selected from the group consisting of F, Cl, Br, and I;

$R_4$=aromatic or aryl, heteroaryl (5-6 membered ring), substituted aromatic or aryl, substituted heteroaryl (5-6 membered ring); wherein said aromatic, aryl or heteroaryl is unsubstituted, mono-, or di-substituted or tri-substituted, wherein the substituents are independently selected from the group consisting of phenyl, $(C_{1-4})$alkyl, $(C_{1-4}$ alkoxy, halogen, $(C_{1-3})$fluoroalkyl, $(C_{1-3})$fluoroalkoxy, and $(C_{3-7})$cycloalkyl, $(C_{3-7})$heterocycloalkyl; wherein the halogen is selected from the group consisting of F, Cl, Br, and I;

$R_5$=$CH_3$, alkyl group, or substituted alkyl; wherein $R_5$ and $R_6$ can be connected as alkyl group to form a $(C_{1-3})$ alkyl bridge cyclic structure;

$R_6$=H, halogen (F, Cl, Br, or I), alkyl group, or substituted alkyl; wherein $R_5$ and $R_6$ can be connected as alkyl group to form a $(C_{1-3})$alkyl bridge cyclic structure; X=$CH_2$, O, or nothing (to provide five membered pyrrolidine ring); wherein the carbon atom at position 2 of the piperidine or pyrrolidine is preferred in absolute (S)-configuration; in contrast, the carbon atom at position 2 of the morpholine ring (when X=O, oxygen) is preferred in absolute (R)-configuration;

Y=NH, O, nothing (to attach $R_4$ directly to $CZ_1Z_2$ group), $CH_2OR_4$, $CH_2$, or $NR_4R_7$ (where $R_7$=H, alkyl);

$Z_1$ and $Z_2$ independently=H, F, $(C_{1-4})$alkyl, $(C_{1-3})$fluoroalkyl, $(C_{1-3})$fluoroalkoxy, or $(C_{2-7})$cycloalkyl; Also wherein:

Fused ring system A-B-J-D-E: five (5)-membered heteroaryl;

Fused ring system B-J-G-K-L: five (5)-membered aromatic or aryl, heteroaryl, cycloalkyl, or heterocycloalkyl;

wherein the preferred groups are:

G=Carbon (C), Nitrogen (N), CH, $CR_2R_3$, $CR_2$, $CR_3$, or O;

K=Carbon, CH, $CR_2R_3$, $CR_2$, $CR_3$, or O; and,

L=O, S, $CR_2R_3$, $CHR_2$, or $CHR_3$.

In some preferred embodiments, this disclosure provides a compounds of formula III, wherein the ring system illustrated by A-B-J-D-E variables in formula (I) fused to the 5-membered ring is preferred as a pyrazolo ring system as represented by embodiment formula (III) herein:

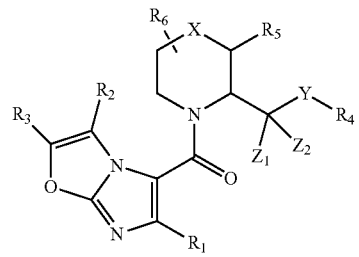

(III)

wherein:
$R_1$=aromatic or aryl, heteroaryl (5-6 membered ring), substituted aromatic or aryl, substituted heteroaryl (5-6 membered ring); when $R_1$ is heteroaryl, it is preferred as a 5- or 6-membered heteroaryl selected from the group consisting of pyrrolyl, pyrazolyl, triazolyl, oxazolyl, thiazolyl, oxadiazolyl, thiophenyl, pyridinyl, pyrimidinyl, pyrazinyl, and pyridazinyl; wherein said aromatic, aryl or heteroaryl is unsubstituted, mono-, or di-substituted, wherein the substituents are independently selected from the group consisting of $(C_{1-4})$ alkyl, $(C_{1-4})$alkoxy, halogen, $(C_{1-3})$fluoroalkyl, $(C_{1-3})$ fluoroalkoxy, and $(C_{3-7})$cycloalkyl; wherein the halogen is optionally selected from the group consisting of F, Cl, Br, and I;

$R_2$, $R_3$=H, halogen (such as F, Cl, Br or I), alkyl group, substituted alkyl, $(C_{1-4})$alkyl, $(C_{1-4})$alkoxy, halogen, $(C_{1-3})$fluoroalkyl, $(C_{1-3})$fluoroalkoxy, and $(C_{3-7})$cycloalkyl; wherein each of $R_2$ and $R_3$ is independently and optionally substituted at each substitutable position with up to 3 substituents independently selected from one or both $R_2$ and $R_3$; wherein the halogen is selected from the group consisting of F, Cl, Br, and I;

$R_4$=aromatic or aryl, heteroaryl (5-6 membered ring), substituted aromatic or aryl, substituted heteroaryl (5-6 membered ring); wherein said aromatic, aryl or heteroaryl is unsubstituted, mono-, or di-substituted or tri-substituted, wherein the substituents are independently selected from the group consisting of phenyl, $(C_{1-4})$alkyl, $(C_{1-4})$alkoxy, halogen, $(C_{1-3})$fluoroalkyl, $(C_{1-3})$fluoroalkoxy, and $(C_{3-7})$cycloalkyl, $(C_3)$heterocycloalkyl; wherein the halogen is selected from the group consisting of F, Cl, Br, and I;

$R_5$=$CH_3$, alkyl group, or substituted alkyl; wherein $R_5$ and $R_6$ can be connected as alkyl group to form a $(C_{1-3})$ alkyl bridge cyclic structure;

$R_6$=H, halogen (F, Cl, Br, or I), alkyl group, or substituted alkyl; wherein $R_5$ and $R_6$ can be connected as alkyl group to form a $(C_{1-3})$alkyl bridge cyclic structure;

X=$CH_2$, O, or nothing (to provide five membered pyrrolidine ring); wherein the carbon atom at position 2 of the piperidine or pyrrolidine is preferred in absolute (S)-configuration; in contrast, the carbon atom at position 2 of the morpholine ring (when X=O, oxygen) is preferred in absolute (R)-configuration;

Y=NH, O, nothing (to attach $R_4$ directly to $CZ_1Z_2$ group), $CH_2OR_4$, $CH_2$, or $NR_4R_7$ (where $R_7$=H, alkyl); and, $Z_1$ and $Z_2$ independently=H, F, $(C_{1-4})$alkyl, $(C_{1-3})$fluoroalkyl, $(C_{1-3})$fluoroalkoxy, or $(C_{2-7})$cycloalkyl.

In some preferred embodiments, this disclosure provides a compounds in which the imidazole fused 5-membered ring is as shown in formula IV:

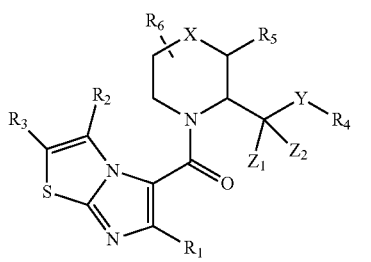

(IV)

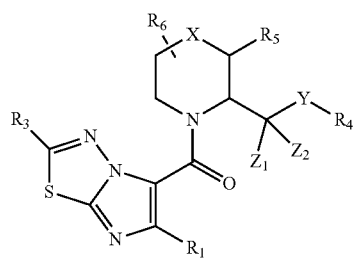

(V)

wherein:
- $R_1$=aromatic or aryl, heteroaryl (5-6 membered ring), substituted aromatic or aryl, substituted heteroaryl (5-6 membered ring); when $R_1$ is heteroaryl, it is preferred as a 5- or 6-membered heteroaryl selected from the group consisting of pyrrolyl, pyrazolyl, triazolyl, oxazolyl, thiazolyl, oxadiazolyl, thiophenyl, pyridinyl, pyrimidinyl, pyrazinyl, and pyridazinyl; wherein said aromatic, aryl or heteroaryl is unsubstituted, mono-, or di-substituted, wherein the substituents are independently selected from the group consisting of $(C_{1-4})$ alkyl, $(C_{1-4})$alkoxy, halogen, $(C_{1-3})$fluoroalkyl, $(C_{1-3})$ fluoroalkoxy, and $(C_{3-7})$cycloalkyl; wherein the halogen is optionally selected from the group consisting of F, Cl, Br, and I;
- $R_2$, $R_3$=H, halogen (such as F, Cl, Br or I), alkyl group, substituted alkyl, $(C_{1-4})$alkyl, $(C_{1-4})$alkoxy, halogen, $(C_{1-3})$fluoroalkyl, $(C_{1-3})$fluoroalkoxy, and $(C_{3-7})$cycloalkyl; wherein each of $R_2$ and $R_3$ is independently and optionally substituted at each substitutable position with up to 3 substituents independently selected from one or both $R_2$ and $R_3$; wherein the halogen is selected from the group consisting of F, Cl, Br, and I;
- $R_4$=aromatic or aryl, heteroaryl (5-6 membered ring), substituted aromatic or aryl, substituted heteroaryl (5-6 membered ring); wherein said aromatic, aryl or heteroaryl is unsubstituted, mono-, or di-substituted or tri-substituted, wherein the substituents are independently selected from the group consisting of phenyl, $(C_{1-4})$alkyl, $(C_{1-4})$alkoxy, halogen, $(C_{1-3})$fluoroalkyl, $(C_{1-3})$fluoroalkoxy, and $(C_{3-7})$cycloalkyl, $(C_{3-7})$heterocycloalkyl; wherein the halogen is selected from the group consisting of F, Cl, Br, and I;
- $R_5$=$CH_3$, alkyl group, or substituted alkyl; wherein $R_5$ and $R_6$ can be connected as alkyl group to form a $(C_{1-3})$ alkyl bridge cyclic structure;
- $R_6$=H, halogen (F, Cl, Br, or I), alkyl group, or substituted alkyl; wherein $R_5$ and $R_6$ can be connected as alkyl group to form a $(C_{1-3})$alkyl bridge cyclic structure;
- X=$CH_2$, O, or nothing (to provide five membered pyrrolidine ring); wherein the carbon atom at position 2 of the piperidine or pyrrolidine is preferred in absolute (S)-configuration; in contrast, the carbon atom at position 2 of the morpholine ring (when X=O, oxygen) is preferred in absolute (R)-configuration;
- Y=NH, O, nothing (to attach $R_4$ directly to $CZ_1Z_2$ group), $CH_2OR_4$, $CH_2$, or $NR_4R_7$ (where $R_7$=H, alkyl); and,
- $Z_1$ and $Z_2$ independently=H, F, $(C_{1-4})$alkyl, $(C_{1-3})$fluoroalkyl, $(C_{1-3})$fluoroalkoxy, or $(C_{2-7})$cycloalkyl.

In some preferred embodiments, this disclosure provides compounds in which the imidazole fused 5-membered ring is as shown in formula V:

wherein:
- $R_1$=aromatic or aryl, heteroaryl (5-6 membered ring), substituted aromatic or aryl, substituted heteroaryl (5-6 membered ring); when $R_1$ is heteroaryl, it is preferred as a 5- or 6-membered heteroaryl selected from the group consisting of pyrrolyl, pyrazolyl, triazolyl, oxazolyl, thiazolyl, oxadiazolyl, thiophenyl, pyridinyl, pyrimidinyl, pyrazinyl, and pyridazinyl; wherein said aromatic, aryl or heteroaryl is unsubstituted, mono-, or di-substituted, wherein the substituents are independently selected from the group consisting of $(C_{1-4})$ alkyl, $(C_{1-4})$alkoxy, halogen, $(C_{1-3})$fluoroalkyl, $(C_{1-3})$ fluoroalkoxy, and $(C_{3-7})$cycloalkyl; wherein the halogen is optionally selected from the group consisting of F, Cl, Br, and I;
- $R_3$=H, halogen (such as F, Cl, Br or I), alkyl group, substituted alkyl, $(C_{1-4})$alkyl, $(C_{1-4})$alkoxy, halogen, $(C_{1-3})$fluoroalkyl, $(C_{1-3})$fluoroalkoxy, and $(C_{3-7})$cycloalkyl; wherein each $R_3$ is independently and optionally substituted at each substitutable position with up to 3 substituents independently selected from one or both $R_2$ and $R_3$; wherein the halogen is selected from the group consisting of F, Cl, Br, and I;
- $R_4$=aromatic or aryl, heteroaryl (5-6 membered ring), substituted aromatic or aryl, substituted heteroaryl (5-6 membered ring); wherein said aromatic, aryl or heteroaryl is unsubstituted, mono-, or di-substituted or tri-substituted, wherein the substituents are independently selected from the group consisting of phenyl, $(C_{1-4})$alkyl, $(C_{1-4})$alkoxy, halogen, $(C_{1-3})$fluoroalkyl, $(C_{1-3})$fluoroalkoxy, and $(C_{3-7})$cycloalkyl, $(C_3)$heterocycloalkyl; wherein the halogen is selected from the group consisting of F, Cl, Br, and I;
- $R_5$=$CH_3$, alkyl group, or substituted alkyl; wherein $R_5$ and $R_6$ can be connected as alkyl group to form a $(C_{1-3})$ alkyl bridge cyclic structure;
- $R_6$=H, halogen (F, Cl, Br, or I), alkyl group, or substituted alkyl; wherein $R_5$ and $R_6$ can be connected as alkyl group to form a $(C_{1-3})$alkyl bridge cyclic structure;
- X=$CH_2$, O, or nothing (to provide five membered pyrrolidine ring); wherein the carbon atom at position 2 of the piperidine or pyrrolidine is preferred in absolute (S)-configuration; in contrast, the carbon atom at position 2 of the morpholine ring (when X=O, oxygen) is preferred in absolute (R)-configuration;
- Y=NH, O, nothing (to attach $R_4$ directly to $CZ_1Z_2$ group), $CH_2OR_4$, $CH_2$, or $NR_4R_7$ (where $R_7$=H, alkyl); and,
- $Z_1$ and $Z_2$ independently=H, F, $(C_{1-4})$alkyl, $(C_{1-3})$fluoroalkyl, $(C_{1-3})$fluoroalkoxy, or $(C_{2-7})$cycloalkyl.

In some preferred embodiments, this disclosure provides a compounds in which the imidazole fused 5-membered ring is as shown in formula VI:

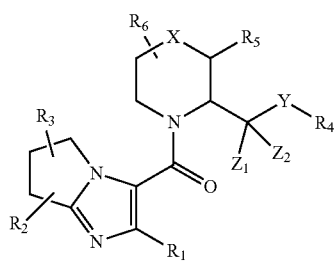

(VI)

wherein:

R$_1$=aromatic or aryl, heteroaryl (5-6 membered ring), substituted aromatic or aryl, substituted heteroaryl (5-6 membered ring); when R$_1$ is heteroaryl, it is preferred as a 5- or 6-membered heteroaryl selected from the group consisting of pyrrolyl, pyrazolyl, triazolyl, oxazolyl, thiazolyl, oxadiazolyl, thiophenyl, pyridinyl, pyrimidinyl, pyrazinyl, and pyridazinyl; wherein said aromatic, aryl or heteroaryl is unsubstituted, mono-, or di-substituted, wherein the substituents are independently selected from the group consisting of (C$_{1-4}$) alkyl, (C$_{1-4}$)alkoxy, halogen, (C$_{1-3}$)fluoroalkyl, (C$_{1-3}$) fluoroalkoxy, and (C$_{3-7}$)cycloalkyl; wherein the halogen is optionally selected from the group consisting of F, Cl, Br, and I;

R$_2$, R$_3$=H, halogen (such as F, Cl, Br or I), alkyl group, substituted alkyl, (C$_{1-4}$)alkyl, (C$_{1-4}$)alkoxy, halogen, (C$_{1-3}$)fluoroalkyl, (C$_{1-3}$)fluoroalkoxy, and (C$_{3-7}$)cycloalkyl; wherein each of R$_2$ and R$_3$ is independently and optionally substituted at each substitutable position with up to 3 substituents independently selected from one or both R$_2$ and R$_3$; wherein the halogen is selected from the group consisting of F, Cl, Br, and I;

R$_4$=aromatic or aryl, heteroaryl (5-6 membered ring), substituted aromatic or aryl, substituted heteroaryl (5-6 membered ring); wherein said aromatic, aryl or heteroaryl is unsubstituted, mono-, or di-substituted or tri-substituted, wherein the substituents are independently selected from the group consisting of phenyl, (C$_{1-4}$)alkyl, (C$_{1-4}$)alkoxy, halogen, (C$_{1-3}$)fluoroalkyl, (C$_{1-3}$)fluoroalkoxy, and (C$_{3-7}$)cycloalkyl, (C$_3$)heterocycloalkyl; wherein the halogen is selected from the group consisting of F, Cl, Br, and I;

R$_5$=CH$_3$, alkyl group, or substituted alkyl; wherein R$_5$ and R$_6$ can be connected as alkyl group to form a (C$_{1-3}$) alkyl bridge cyclic structure;

R$_6$=H, halogen (F, Cl, Br, or I), alkyl group, or substituted alkyl; wherein R$_5$ and R$_6$ can be connected as alkyl group to form a (C$_{1-3}$)alkyl bridge cyclic structure;

X=CH$_2$, O, or nothing (to provide five membered pyrrolidine ring); wherein the carbon atom at position 2 of the piperidine or pyrrolidine is preferred in absolute (S)-configuration; in contrast, the carbon atom at position 2 of the morpholine ring (when X=O, oxygen) is preferred in absolute (R)-configuration;

Y=NH, O, nothing (to attach R$_4$ directly to CZ$_1$Z$_2$ group), CH$_2$OR$_4$, CH$_2$, or NR$_4$R$_7$ (where R$_7$=H, alkyl); and, Z$_1$ and Z$_2$ independently=H, F, (C$_{1-4}$)alkyl, (C$_{1-3}$)fluoroalkyl, (C$_{1-3}$)fluoroalkoxy, or (C$_{2-7}$)cycloalkyl.

In more preferred embodiments, this disclosure provides the compounds of formula I, II, III, IV, V or VI shown below:

Example 1

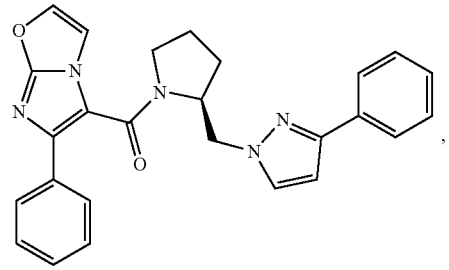

Example 2

Example 3

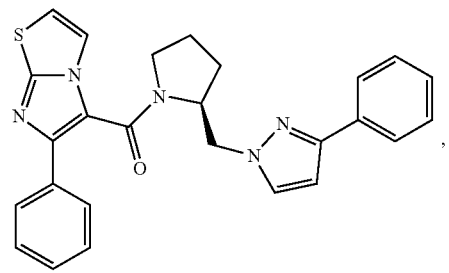

Example 4

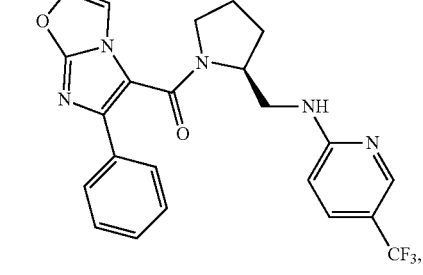

Example 5

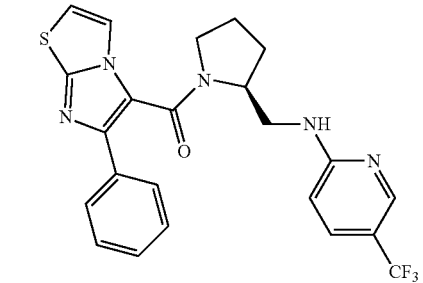

Example 6
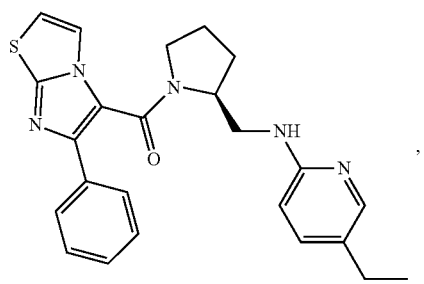
Example 7
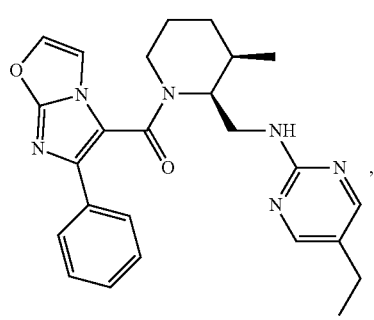
Example 8
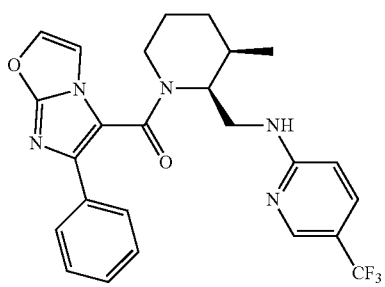
Example 9
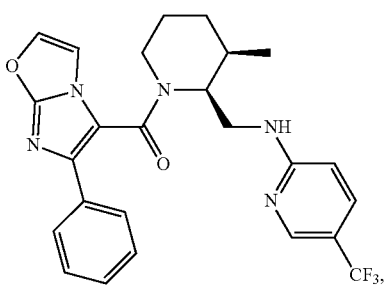
Example 10
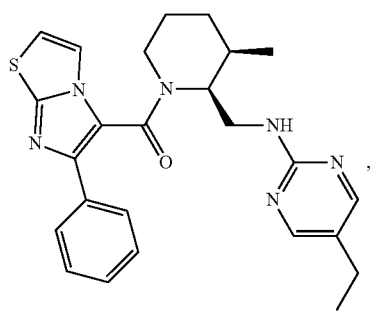
Example 11
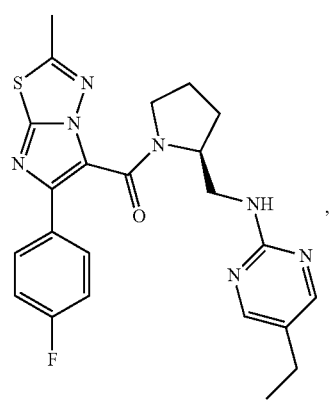
Example 12
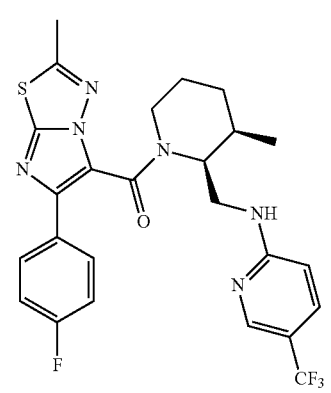
Example 13
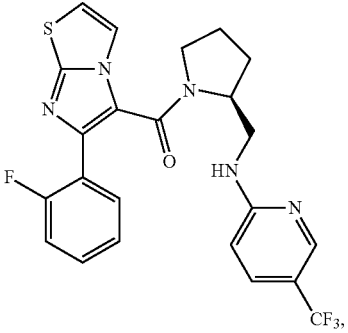
Example 14
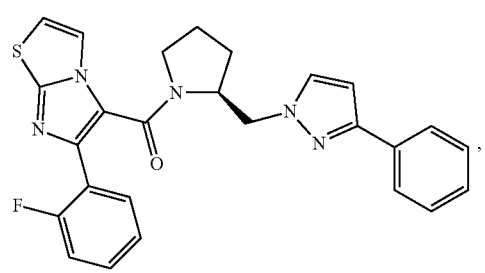

Example 15

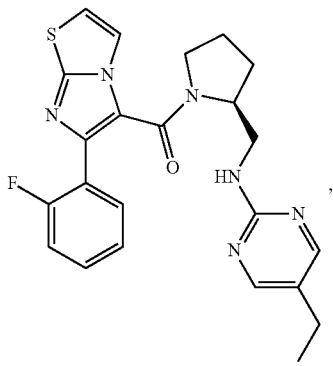

Example 16

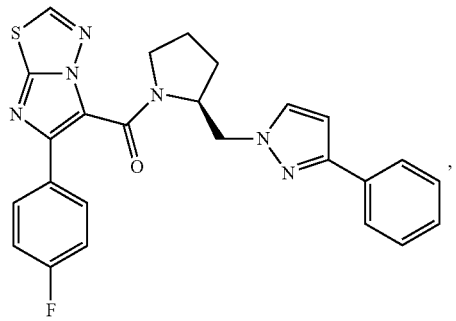

Example 17

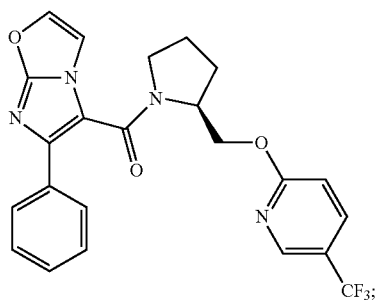

Example 18 or a pharmaceutically acceptable salt, hydrate, solvate, polymorph, isomer, or combination thereof.

The term "alkyl" as used herein means a linear or branched carbon chain (e.g., having the general formula $C_{(n)}H_{(2n+1)}$) including but not limited to any of $C_1$-$C_{100}$ (e.g., methyl, ethyl, propyl, and the like). The term "fluroalkyl" as used herein means an alkyl substituted by at least one flourine atom. The term "alkoxy" as used herein means an alkyl bonded to oxygen (i.e., R—O). The term "fluoroalkoxy" as used herein means an alkoxy substituted by at least one fluorine atom. The term "heterocycloalkyl" as used herein means a cycloalkyl comprising at least one heteroatom (e.g., N and/or O) within the cyclic ring thereof. The term "aryl" as used herein means a monocyclic or bicyclic carbocyclic aromatic or aryl ring system. Phenyl is an example of a monocyclic aromatic or aryl ring system. The term "heteroaryl" as used herein means a monocyclic or bicyclic aromatic or aryl ring system having 1 to 3 heteroatom or heteroatom groups in each ring selected from O, N, NH or S in a chemically stable arrangement. In such a bicyclic aromatic or aryl ring system embodiment of "heteroaryl": both rings may be aromatic or aryl; and one or both rings may contain said heteroatom or heteroatomgroups. Examples of heteroaryl rings include 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl). The terms "cycloalkyl" or "cycloalkenyl" refers to a monocyclic or fused or ($C_3$)alkyl bridged bicyclic carbocyclic ring system that is not aromatic or aryl. Cycloalkenyl rings have one or more units of unsaturation. Preferred cycloalkyl or cycloalkenyl groups include cyclopropyl, cyclobutyl, cyclopentyl, cyclohexyl, cyclohexenyl, cycloheptyl, cycloheptenyl, norbornyl, adamantly and decalinyl. While "halogen" can be F, Cl, Br or I, preferred embodiments are those in which halogen is F, Cl or Br. The term "substituted" as used herein means, for a particular group (e.g., alkyl, aryl, heteroaryl, aromatic), the replacement of one functional group by another (e.g., the substitution of an alkyl hydrogen by fluorine to provide fluoroalkyl).

Any embodiment given herein is also intended to represent unlabeled forms as well as isotopically labeled forms of the compounds, unless otherwise indicated. Isotopically labeled compounds have structures depicted by the formulas given herein except that one or more atoms are replaced by an atom having a selected atomic mass or mass number. Examples of isotopes that can be incorporated into compounds of this disclosure include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$, respectively. The disclosure includes various isotopically labeled compounds as defined herein, for example those into which radioactive isotopes, such as $^3H$, $^{13}C$, and $^{14}C$, are present. Such isotopically labelled compounds are useful in metabolic studies (preferably with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly preferred for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure also relates to all stereoisomeric forms such as enantiomeric and diastereoisomeric forms of the compounds or mixtures thereof (including all possible mixtures of stereoisomers). See, e.g., WO01/062726 (see also US 2017/0022208 A1, US 2017/0253603 A2). Furthermore, multiple substituents on a piperidinyl or pyrrolidinyl ring can also be in either cis or trans relationship to each other with respect to the plane of the piperidinyl or the pyrrolidinyl ring. Such forms or geometric isomers, although not explicitly indicated in the formulae described herein, are intended to be included within the scope of the present disclosure. With respect to the methods and compositions of the present disclosure, reference to a compound or compounds is intended to encompass that compound in each of its possible isomeric forms and mixtures thereof unless the particular isomeric form is referred to specifically.

Pharmaceutically acceptable salts is used herein to refer to an agent or a compound according to the invention that is a therapeutically active, non-toxic base and acid salt form of the compounds. The acid addition salt form of a compound that occurs in its free form as a base can be obtained by treating said free base form with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclic, salicylic, p-aminosalicylic, pamoic and the like. See, e.g., WO 01/062726 (see also US 2017/0022208 A1, US 2017/0253603 A2).

Compounds containing acidic protons may be converted into their therapeutically active, non-toxic base addition salt form, e. g., metal or amine salts, by treatment with appropriate organic and inorganic bases. Appropriate base salt forms include, for example, ammonium salts, alkali and alkaline earth metal salts, e. g., lithium, sodium, potassium, magnesium, calcium salts and the like, salts with organic bases, and salts with amino acids such as, for example, arginine, lysine and the like. Conversely, said salt forms can be converted into the free forms by treatment with an appropriate base or acid. Compounds and their salts can be in the form of a solvate, which is included within the scope of the present disclosure. Such solvates include for example hydrates, alcoholates and the like.

The compounds of this disclosure also include prodrugs. The term "prodrug" is a recognized art in the field and is intended to encompass compounds or agents which, under physiological conditions, are converted into orexin antagonists. A common method for making a prodrug is to select moieties which are hydrolyzed or metabolized under physiological conditions to provide the desired compound or agent. In other embodiments, the prodrug is converted by an enzymatic activity of the host animal to an orexin antagonist.

This disclosure also includes isotopically labelled, especially $^2$H (deuterium) labelled compounds of all formulas, which compounds are identical to the compounds of all formulas described herein except that one or more atoms have each been replaced by an atom having the same atomic number but an atomic mass different from the atomic mass usually found in nature. Isotopically labelled, especially $^2$H (deuterium) labelled compounds of all formulas and salts thereof are within the scope of this disclosure. Substitution of hydrogen with the heavier isotope $^2$H (deuterium) may lead to greater metabolic stability resulting e.g., in increased in-vivo half-life or reduced dosage requirements, or may lead to reduced inhibition of cytochrome P450 enzymes, resulting e.g., in an improved safety profile. In another aspects of embodiment of the invention, the compounds of all formulas are not isotopically labelled. However, isotopically labelled compounds of all formula could be prepared by anyone skilled in the art in analogy to the methods described hereinafter but using the appropriate isotopic variation of suitable reagents or starting materials.

In some embodiments, this disclosure provides methods for preparing the compounds disclosed herein. In preferred embodiments, the compounds of this disclosure are prepared using the methods described in the Examples below, or suitable variants thereof as would be understood by those of ordinary skill in the art. In some embodiments, the methods can comprise the use of intermediate compounds such as those disclosed herein, with specific uses of such intermediates being described in more detail in the Examples section. Thus, in some embodiments, this disclosure provides intermediates (e.g., Intermediates A through M shown in the Examples section below) that can be used to produce the compounds of the formulas disclosed herein, such as but not limited to Examples 1 through 18. In some embodiments, this disclosure also provides intermediates used to produce intermediates A through M. In preferred embodiments, such intermediates can include Intermediate A and/or Intermediate A1; Intermediate B and/or Intermediate B1; Intermediate C and/or Intermediate C1; Intermediate D, Intermediate D1, and/or Intermediate D2; Intermediate E and/or Intermediate E1; Intermediate F or Intermediate F1; Intermediate G, Intermediate G1, and/or Intermediate G2; Intermediate H and/or Intermediate H1; Intermediate I or Intermediate I1; Intermediate J; Intermediate K; Intermediate L and/or Intermediate L1; and/or, Intermediate M or Intermediate M1.

In some embodiments, Intermediate J and Intermediate G can be used to produce a compound of Example 1. In some embodiments, Intermediate D and Intermediate G can be used to produce a compound of Example 2. In some embodiments, Intermediate J and Intermediate A can be used to produce a compound of Example 3. In some embodiments, Intermediate D and Intermediate A can be used to produce a compound of Example 4. In some embodiments, Intermediate J and Intermediate B can be used to produce a compound of Example 5. In some embodiments, Intermediate D and Intermediate B can be used to produce a compound of Example 6. In some embodiments, Intermediate J and Intermediate C can be used to produce a compound of Example 7. In some embodiments, Intermediate J and Intermediate E can be used to produce a compound of Example 8. In some embodiments, Intermediate D and Intermediate E can be used to produce a compound of Example 9. In some embodiments, Intermediate D and Intermediate C can be used to produce a compound of Example 10. In some embodiments, Intermediate L and Intermediate B can be used to produce a compound of Example 11. In some embodiments, Intermediate L and Intermediate E can be used to produce a compound of Example 12. In some embodiments, Intermediate F and Intermediate A can be used to produce a compound of Example 13. In some embodiments, Intermediate F and Intermediate G can be used to produce a compound of Example 14. In some embodiments, Intermediate F and Intermediate B can be used to produce a compound of Example 15. In some embodiments, Intermediate M and Intermediate G can be used to produce a compound of Example 16. In some embodiments, Intermediate J and Intermediate H can be used to produce a compound of Example 17. In some embodiments, Intermediate J and Intermediate I can be used to produce a compound of Example 18. As used herein, the phrase "can be used" is equivalent to "can be reacted with" (e.g., as shown in the Examples section below). While such methods for preparing the compounds of Examples 1-18 can be used, those of ordinary skill in the art would understand other methods can also be used.

The compounds of this disclosure can be used for various in vivo methods of treatment, the compounds can also be used in vitro to inhibit Orexin receptors type 1 and/or 2 (i.e., Orexin receptors type 1 and/or 2 antagonists). For instance, in some embodiments, Chinese hamster ovary (CHO) cells expressing the human orexin-1 receptor and/or the human orexin-2 receptors can be incubated with one or more antagonists or potential antagonists (e.g., compounds of Examples 1-18) and one or more indicator compounds (e.g., fluorescent calcium indicator such as fluo-4 AM) along with one or more agonists, and antagonist activity measured using a Fluorescent Imaging Plate Reader (FLIPR Tetra, Molecular Devices). Antagonistic activity can be recorded as the 50% inhibitory concentration ($IC_{50}$) values. Other suitable methods for identifying antagonistic compounds are also known to those of ordinary skill in the art.

Thus, in some embodiments, his disclosure provides compounds that can be used for in vivo treatments of various disease states, and/or in vitro (e.g., as Orexin receptors type 1 and/or 2 antagonists). In some embodiments, this disclosure provides compounds of formulas I, II, III, IV, IV, and/or VI, or as may be otherwise disclosed and/or contemplated herein:

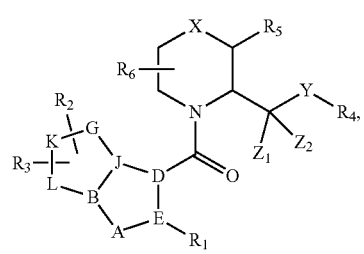

(I)

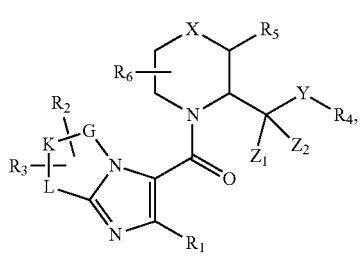

(II)

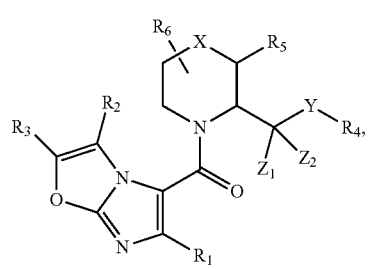

(III)

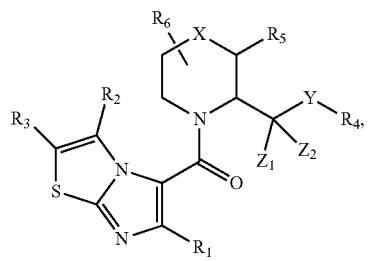

(IV)

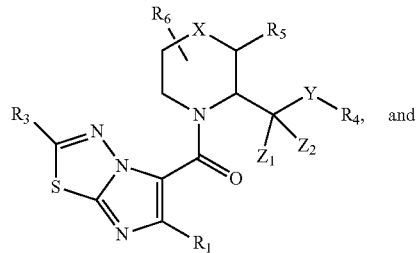

(V)

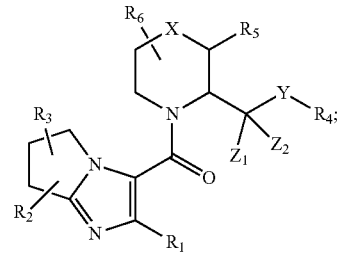

(VI)

or a pharmaceutically acceptable salt, hydrate, solvate, polymorph, isomer, or combination thereof, wherein:

$R_1$ is independently is selected from the group consisting of aromatic, aryl, five- or six-member heteroaryl, substituted aromatic, substituted aryl, substituted five- or six-member heteroaryl; optionally wherein the heteroaryl is selected from the group consisting of pyrrolyl, pyrazolyl, triazolyl, oxazolyl, thiazolyl, oxadiazolyl, thiophenyl, pyridinyl, pyrimidinyl, pyrazinyl, and pyridazinyl; wherein said aromatic, aryl or heteroaryl is unsubstituted, mono-substituted by one $R_1$ substituent, or di-substituted by two $R_1$ substituents, wherein each $R_1$ substituent is independently selected from the group consisting of $(C_{1-4})$alkyl, $(C_{1-4})$alkoxy, halogen, $(C_{1-3})$fluoroalkyl, $(C_{1-3})$fluoroalkoxy, and $(C_{3-7})$cycloalkyl; wherein the halogen is optionally selected from the group consisting of F, Cl, Br, and I;

$R_2$ and $R_3$ are independently selected from the group consisting of H, halogen, alkyl, substituted alkyl, $(C_{1-4})$alkyl, $(C_{1-4})$alkoxy, halogen, $(C_{1-3})$fluoroalkyl, $(C_{1-3})$fluoroalkoxy, and $(C_{3-7})$cycloalkyl; wherein each of $R_2$ and $R_3$ is independently and optionally substituted at each substitutable position with up to three $R_2$-$R_3$ substituents, wherein each $R_2$-$R_3$ substituent is independently selected from the group consisting of H, halogen, alkyl, substituted alkyl, $(C_{1-4})$alkyl, $(C_{1-4})$alkoxy, halogen, $(C_{1-3})$fluoroalkyl, $(C_{1-3})$fluoroalkoxy, and $(C_{3-7})$cycloalkyl; wherein the halogen is selected from the group consisting of F, Cl, Br, and I;

$R_4$ is selected from the group consisting of aromatic, aryl, five- or six-member heteroaryl, substituted aromatic, substituted aryl, substituted five- or six-member heteroaryl; wherein said aromatic, aryl or heteroaryl is unsubstituted, mono-substituted by one $R_{4a}$ substituent, di-substituted by two $R_{4a}$ substituents, or tri-substituted by three $R_{4a}$ substituents, wherein each $R_{4a}$ substituent is independently selected from the group consisting of phenyl, $(C_{1-4})$alkyl, $(C_{1-4})$alkoxy, halogen, $(C_{1-3})$fluoroalkyl, $(C_{1-3})$fluoroalkoxy, $(C_{3-7})$cycloalkyl, and $(C_{3-7})$heterocycloalkyl; wherein the halogen is selected from the group consisting of F, Cl, Br, and I;

$R_5$ is selected from the group consisting of $CH_3$, alkyl group, and substituted alkyl;

$R_6$ is selected from the group consisting of H, halogen, alkyl group, and substituted alkyl; wherein the halogen is selected from the group consisting of F, Cl, Br, and I;

$R_5$ and $R_6$ are optionally connected as alkyl group to form a $(C_{1-3})$alkyl bridge cyclic structure;

X is absent to provide a pyrrolidine ring, $CH_2$ to provide a piperidine ring, or O to provide a morpholine ring; wherein the carbon atom at position 2 of the piperidine or pyrrolidine is optionally in absolute (S)-configuration; and wherein the carbon atom at position 2 of the morpholine ring is optionally in absolute (R)-configuration;

Y is absent of selected from the group consisting of NH, O, $CH_2OR_4$, $CH_2$, and $NR_4R_7$ where $R_7$ is H or alkyl; and, $Z_1$ and $Z_2$ are each independently selected from the group consisting of H, F, $(C_{1-4})$alkyl, $(C_{1-3})$fluoroalkyl, $(C_{1-3})$fluoroalkoxy, and $(C_{2-7})$cycloalkyl;

and wherein:

A-B-J-D-E is a five-member heteroaryl;

B-J-G-K-L is a five-member ring selected from the group consisting of aromatic, aryl, heteroaryl, cycloalkyl, and heterocycloalkyl;

and wherein, optionally:

A is N; and/or,

B is C or N; and/or,

J is C or N; and/or,

D is C; and/or,

E is C; and/or,

G is selected from the group consisting of C, N, CH, $CR_2R_3$, $CR_2$, $CR_3$, and O;

K is selected from the group consisting of C, CH, $CR_2R_3$, $CR_2$, $CR_3$, and O; and, L is selected from the group consisting of O, S, $CR_2R_3$, $CHR_2$, and $CHR_3$.

In some embodiments, this disclosure provides the preferred compounds of formulas I, II, III, IV and V shown below and in Examples 1-18:

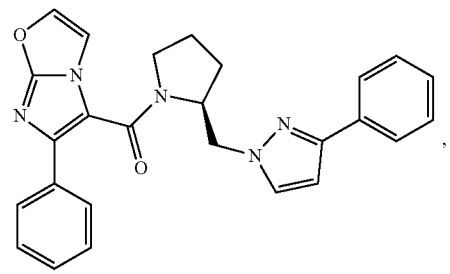

Example 1

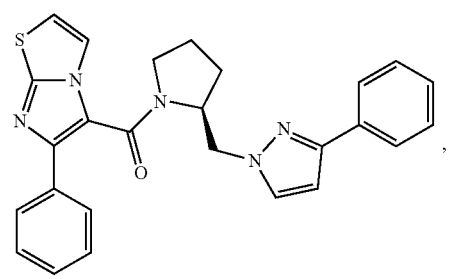

Example 2

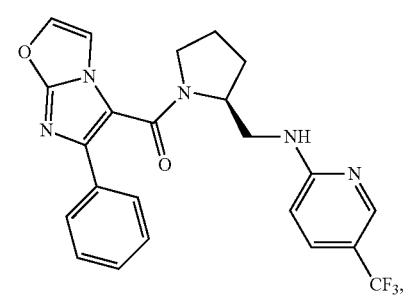

Example 3

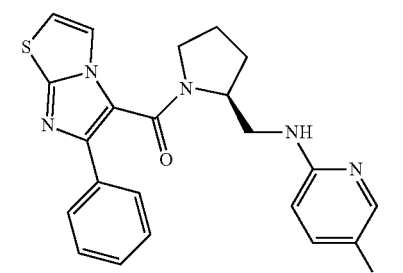

Example 4

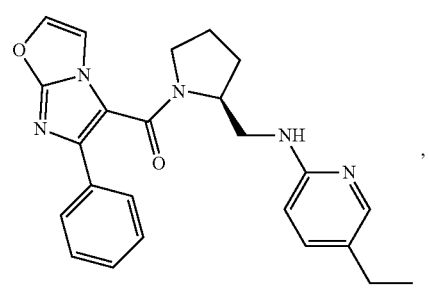

Example 5

Example 6
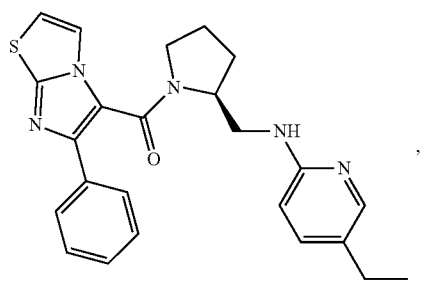
Example 7
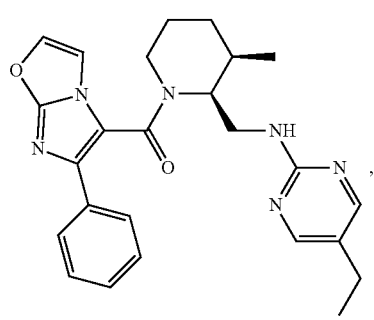
Example 8
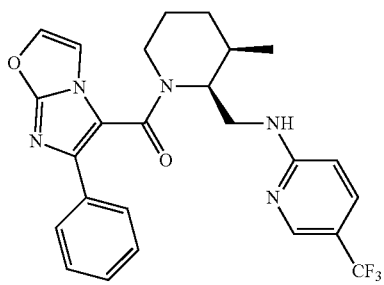
Example 9
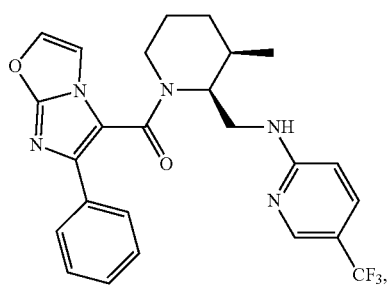
Example 10
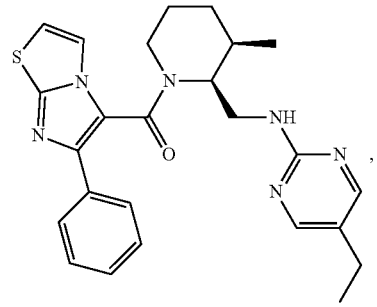
Example 11
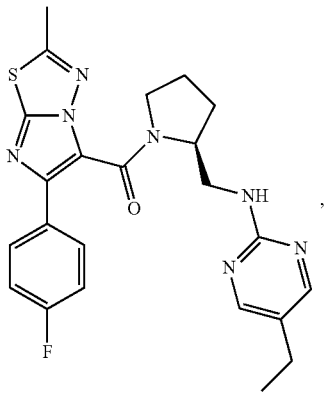
Example 12
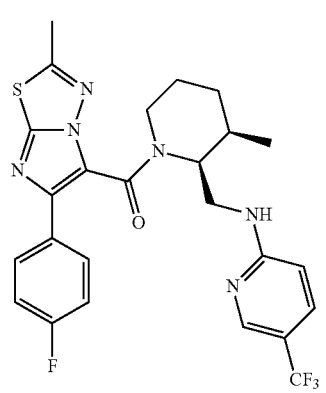
Example 13
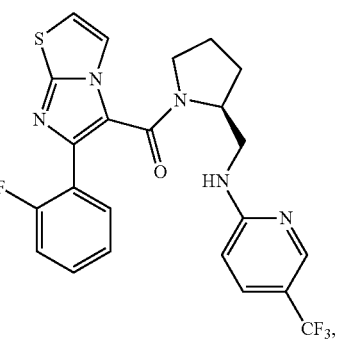
Example 14
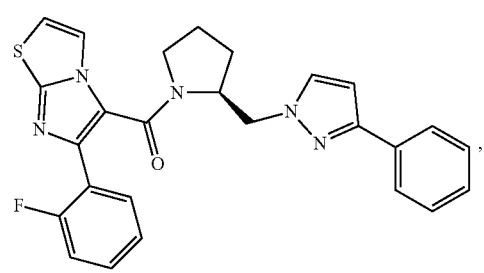

Example 15

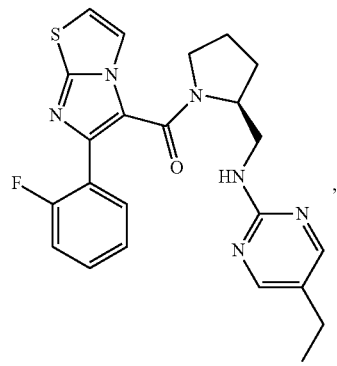

Example 16

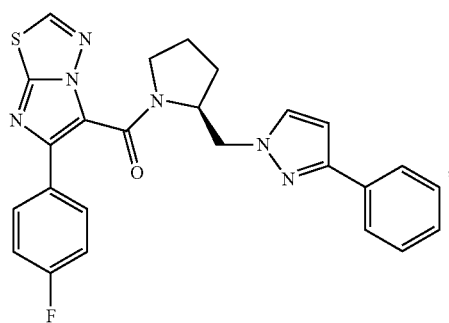

Example 17

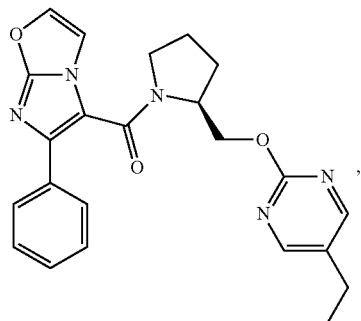

Example 18

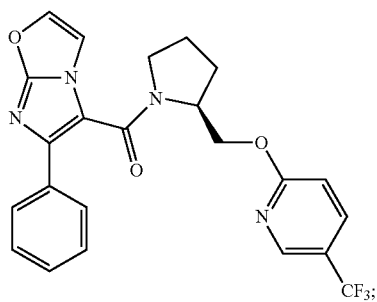

or a pharmaceutically acceptable salt, hydrate, solvate, polymorph, isomer, or combination thereof.

In some embodiments, this disclosure provides a composition comprising any one or more of such a compound, and/or pharmaceutically acceptable salt, hydrate, solvate, polymorph, isomer, or combination thereof. In some embodiments, this disclosure provides a pharmaceutical composition comprising a compound, pharmaceutically acceptable salt, hydrate, solvate, polymorph, isomer, or combination thereof; and at least one pharmaceutically acceptable excipient, carrier, adjuvant, or vehicle. In some embodiments, this disclosure provides a therapeutically effective amount of such a compound, or a pharmaceutically acceptable salt, hydrate, solvate, polymorph, isomer, or combination thereof. In some embodiments, this disclosure provides such a pharmaceutical composition further comprises at least one second therapeutic agent. In some embodiments, this disclosure provides methods of preventing or treating a condition selected from the group consisting of a central nervous system (CNS) disorder, substance addiction, dependence, panic, anxiety, depression, posttraumatic stress disorder (PTSD), neurodegeneration, autism, schizophrenia, and Alzheimer disease (AD) in a subject in need thereof, by administering to the subject any of such one or more compounds and/or composition comprising one or more of such compounds, or pharmaceutically acceptable salt, hydrate, solvate, polymorph, isomer, or combination thereof. In some embodiments, the methods can include administering a composition comprising a therapeutically effective amount of the compound, pharmaceutically acceptable salt, hydrate, solvate, polymorph, isomer, or combination thereof. In some embodiments, the composition comprises a pharmaceutically acceptable salt or isotope of such a compound. In some embodiments, the composition can comprise an unlabeled form of the compound or an isotopically labeled form of the compound in which the compound has a structure depicted by the formula wherein one or more atoms are replaced by an atom having a selected atomic mass or mass number. In some embodiments, this disclosure provides for the use of a compound, pharmaceutically acceptable salt, hydrate, solvate, polymorph, isomer, or combination thereof, disclosed herein in the preparation of a medicament for preventing and/or treating a condition selected from the group consisting of a central nervous system (CNS) disorder, substance addiction, dependence, panic, anxiety, depression, posttraumatic stress disorder (PTSD), neurodegeneration, autism, schizophrenia, and Alzheimer disease (AD) in a subject in need thereof. In some embodiments, the use can include a composition comprises a therapeutically effective amount of the compound, pharmaceutically acceptable salt, hydrate, solvate, polymorph, isomer, or combination thereof. In some embodiments, such use can comprise a composition a pharmaceutically acceptable salt or isotope of the compound. In some embodiments, such use can comprise a composition comprises an unlabeled form of the compound or an isotopically labeled form of the compound in which the compound has a structure depicted by the formula wherein one or more atoms are replaced by an atom having a selected atomic mass or mass number. This disclosure also provides intermediates of the compounds disclosed herein as well as methods for preparing the same. In some embodiments, such methods for preparing can include using any of the intermediates disclosed herein (e.g., any one or more of Intermediates A-J). Other embodiments are also contemplated here as would be understood by those of ordinary skill in the art.

The disclosure also provides pharmaceutical compositions comprising one or more compounds of this disclosure (or the like, such as a pharmaceutically acceptable salt thereof) (i.e., as an active agent, as a therapeutic agent), and one or more pharmaceutically acceptable carriers or excipients. A pharmaceutical composition contains a therapeutically effective amount of one or more of such compounds or the like (i.e., active agent(s)), or an appropriate fraction thereof. A composition can optionally contain an additional active agent. In some embodiments, a peptide product is at least about 90%, 95% or 98% pure. Pharmaceutically acceptable excipients and carriers include pharmaceutically acceptable substances, materials and vehicles. Non-limiting examples of types of excipients include liquid and solid fillers, diluents, binders, lubricants, glidants, surfactants, dispersing agents, disintegration agents, emulsifying agents, wetting agents, suspending agents, thickeners, solvents, isotonic agents, buffers, pH adjusters, absorption-delaying agents, stabilizers, antioxidants, preservatives, antimicrobial agents, antibacterial agents, antifungal agents, chelating agents, adjuvants, sweetening agents, flavoring agents, coloring agents, encapsulating materials and coating materials. The use of such excipients in pharmaceutical formulations is known in the art. For example, conventional vehicles and carriers include without limitation oils (e.g., vegetable oils such as olive oil and sesame oil), aqueous solvents (e.g., saline, buffered saline (e.g., phosphate-buffered saline [PBS]) and isotonic solutions (e.g., Ringer's solution)}, and organic solvents (e.g., dimethyl sulfoxide and alcohols [e.g., ethanol, glycerol and propylene glycol]). Except insofar as any conventional excipient or carrier is incompatible with a peptide product, the disclosure encompasses the use of conventional excipients and carriers in formulations containing a peptide product. See, e.g., Remington: The Science and Practice of Pharmacy, 21st Ed., Lippincott Williams & Wilkins (Philadelphia, Pennsylvania) (2005); Handbook of Pharmaceutical Excipients, 5th Ed., Rowe et ah, Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Pre-formulation and Formulation, Gibson, Ed., CRC Press (Boca Raton, Florida) (2004). The appropriateness of a particular formulation can depend on various factors, such as the route of administration chosen. Potential routes of administration of a pharmaceutical composition comprising the compounds or the like disclosed herein can include, without limitation oral, parenteral (including intradermal, subcutaneous, intramuscular, intravascular, intravenous, intra-arterial, intraperitoneal, intracavitary and topical), topical (including transdermal, transmucosal, intranasal (e.g., by nasal spray or drop), ocular (e.g., by eye drop), pulmonary (e.g., by oral or nasal inhalation), buccal, sublingual, rectal (e.g., by suppository), vaginal (e.g., by suppository), and/or other suitable route.

The term "therapeutically effective amount" refers to an amount of a compound that, when administered to a subject, is sufficient to prevent, reduce the risk of developing, delay the onset of, slow the progression of or cause regression of the medical condition being treated, or to alleviate to some extent the medical condition or one or more symptoms or complications of that condition, at least in some fraction of the subjects taking that compound. The term "therapeutically effective amount" also refers to an amount of a compound that is sufficient to elicit the biological or medical response of a cell, tissue, organ or human which is sought by a medical doctor or clinician. The terms "treat," "treating" and "treatment" include alleviating, ameliorating, inhibiting the progress of, reversing or abrogating a medical condition or one or more symptoms or complications associated with the condition, and alleviating, ameliorating or eradicating one or more causes of the condition. Reference to "treatment" of a medical condition includes prevention of the condition. The terms "prevent", "preventing" and "prevention" include precluding, reducing the risk of developing and delaying the onset of a medical condition or one or more symptoms or complications associated with the condition. The term "medical conditions" (or "conditions" for brevity) includes diseases and disorders. The terms "diseases" and "disorders" are used interchangeably herein.

Throughout this specification, the word "comprise" or variations such as "comprises" or "comprising" will be understood to imply the inclusion of a stated integer (or components) or group of integers (or components), but not the exclusion of any other integer (or components) or group of integers (or components). The singular forms "a," "an," and "the" include the plurals unless the context clearly dictates otherwise. The symbol "=" when used in describing a formula means "is". The term "including" is used to mean "including but not limited to "Including" and "including but not limited to" are used interchangeably. The term "agent" is used herein to denote a chemical compound (such as an organic or a mixture of chemical compounds). Agents include, for example, agents that are known with respect to structure, and their orexin antagonist activities of such agents may render them suitable as "therapeutic agents" in the methods and compositions disclosed herein. In addition, those of ordinary skill in the art recognize that it is common to use the following abbreviations, which may have been used herein and are defined as follows:

Me: methyl
Et: ethyl
t-Bu: tert-butyl
Ar: aryl
Ph: phenyl
BINAP: 2,2'-bis(diphenylphosphino)-1,1'-binaphthyl
Bn: benzyl
Ac: acetyl
Boc: tert-butyloxy carbonyl
BSA: bovine serum albumin
CbzCl: benzylchloroformate
CDI: carbonyl diimidazole
DCM: dichloromethane
DCE: dichloroethane
DEAD: diethylazodicarboxylate
DIPEA: N,N-diisopropylethylamine
DMF: N,N-dimethylformamide
DMSO: dimethylsulfoxide
$CH_2Cl_2$: dichloromethane
EDC: N-(3-Dimethylaminopropyl)-N'-ethylcarbodiimide
$Et_3N$: triethylamine
EtOAc: ethyl acetate
EtOH: ethanol
HCl: hydrogen chloride
HOAt: 1-hydroxy-7-aza-10-benzotriazole
HOBT: hydroxybenzotriazole hydrate
LCMS: Liquid Chromatography Mass Spectrometry
HPLC: High Performance Liquid Chromatography
Hunig's base: N,N-diisopropylethylamine
MeOH: methanol
$MgSO_4$: magnesium sulfate
MTBE: methyl tert-butyl ether
$NaHCO_3$: sodium bicarbonate
Na2CO3: sodium carbonate
K2CO3: potassium carbonate
NaOH: sodium hydroxide
NMM: N-methylmorpholine
$PtO_2$: Platinum oxide
Pd: Palladium
Pd/C: Palladium over carbon
PyClu: 1-(chloro-1pyrrolidinylmethylene)pyrrolidiniumhexafluorophosphate
RT or rt: room temperature
$SOCl_2$: thionyl chloride
THF: tetrahydrofuran
TFA: trifluoroacetic acid X-Phos: 2-(dicyclohexyl-phosphino)-2',4',6'-triisopropyl-biphenyl
HATU: (1-[Bis(dimethylamino)methylene]-1H-1,2,3-triazolo[4,5-b]pyridinium 3-oxid hexafluorophosphate
NMR: Nuclear Magnetic Resonance
ESI: Electrospray Ionization
MS: Mass spectrometry
reaction: reaction All references cited within this disclosure are hereby incorporated by reference in their entirety. Certain embodiments are further described in the following examples. These embodiments are provided as examples only and are not intended to limit the scope of the claims in any way.

EXAMPLES

I. General Synthetic Methods & Procedures

A. General

All temperatures are stated in ° C. Compounds for which synthetic procedures are not given herein, commercially available starting materials were used as received without further purification. Unless otherwise specified, all reactions were carried out in oven-dried glassware under an atmosphere of nitrogen. Compounds were purified by flash column chromatography on silica gel or by preparative HPLC. Compounds described in the invention are characterized by LC-MS data (retention time $t_R$ is given in min; molecular weight obtained from the mass spectrum is given in g/mol) using the conditions listed below.

LC-MS Under Acidic Conditions

Method A: Agilent 1100 series with mass spectrometry detection (MS: Agilent single quadrupole LC/MS system). Column: Zorbax SB (3.5 μm, 4.6×150 mm). Conditions: MeCN (0.1% FA) [gradient eluent A]; water (0.1% FA) [gradient eluent B]. Gradient: 95% B+5% B over 5 min (flow: 0.8 ml/min). Detection: UV 280/254 nm+MS.

Method B: Agilent 1100 series with mass spectrometry detection (MS: Agilent single quadrupole). Column: X-Bridge C18 (3.5 μm, 4.6×150 mm). Conditions: MeCN (0.1% FA) [gradient eluent A]; water (0.1% FA) [gradient eluent B]. Gradient: 95% B+5% B over 5 min (flow: 0.8 ml/min). Detection: UV 280/254 nm+MS.

In general, the compounds of this disclosure may be prepared by methods known to those skilled in the art and contemporary technologies in the field. Schemes 1-4 below illustrate synthetic routes to the compounds of this disclosure. Other equivalent schemes, which will be readily apparent to the ordinary skilled synthetic organic or medicinal chemist may alternatively be used to synthesize various portions of the molecules as illustrated by the general schemes described herein.

B. Intermediates Synthesis

1. Synthesis of Intermediate A:

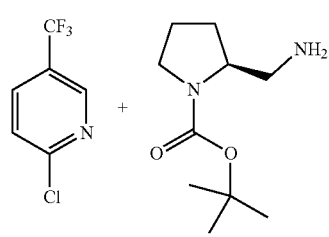

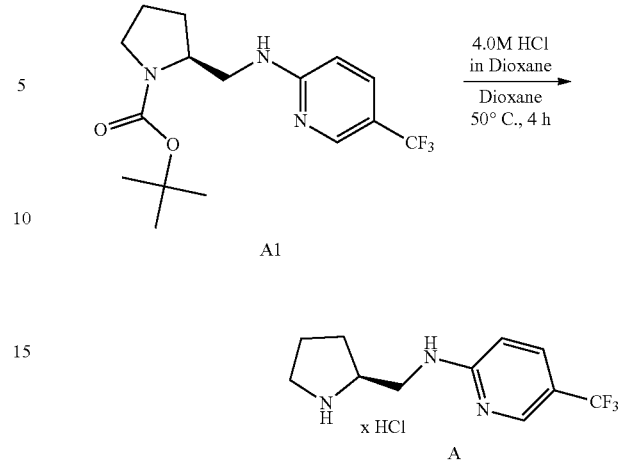

Step 1: Synthesis of Compound A1: 2-Chloro-5-trifluoromethyl-pyridine (0.33 g, 1.82 mmol) and (S)-1-Boc-2-(aminomethyl)-pyrrolidine (0.36 g, 1.81 mmol) were dissolved in dry DMSO (5.0 mL). The DIPEA (1.6 mL, 9.1 mmol) was added and reaction mixture was stirred at 100° C. temperature for 4 h. TLC shows product formation. The reaction mixture was diluted with water. The product was extracted with ethyl acetate. The combined ethyl acetate layer was washed with water followed by brine. The organic layer was separated and dried over anhydrous sodium sulfate. The evaporation of solvent gave crude product. The crude product was purified by ISCO combi-flash chromatography system, mobile phase: EtOAc:Hexane gradient. The desired liquid product was isolated 0.24 g (yield 39.0%). MS (ESI) mass calcd. for $C_{16}H_{22}F_3N_3O_2$, 345.0; m/z found 346.1 $[M+H]^+$.

Step 2: Synthesis of Intermediate A: Compound A1 (0.24 g, 0.71 mmol) were dissolved in dry dioxane (3.0 mL). The 4.0 M HCl solution in dioxane (1.77 mL, 7.08 mmol) was added and reaction mixture was stirred at 50° C. temperature for 4 h. LCMS shows product formation m/z 246. The reaction mixture was concentrated under reduced pressure to obtain solid product (0.19 g, yield 78.4%). MS (ESI) mass calcd. for $C_{11}H_{14}F_3N_3$, 245.2; m/z found 246.0 $[M+H]^+$, $^1H$ NMR (400 MHz, CHLOROFORM-d) δ ppm 1.76-2.01 (m, 1H) 2.01-2.15 (m, 1H) 2.15-2.28 (m, 1H) 2.36 (br s, 1H) 3.25-3.46 (br s, 1H) 3.48 (br s, 1H) 4.04 (br s, 2H) 4.31 (br s, 1H) 7.47 (br s, 1H) 7.86 (br s, 1H) 8.19 (br s, 1H) 9.41-10.42 (br s, 1H).

2. Synthesis of Intermediate B:

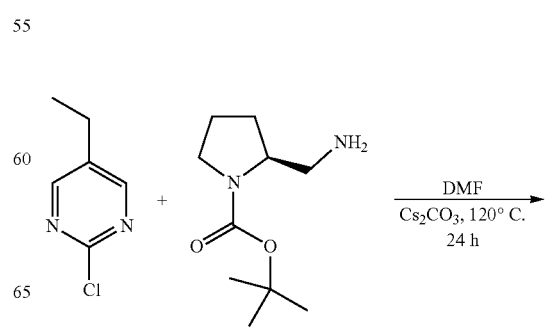

-continued

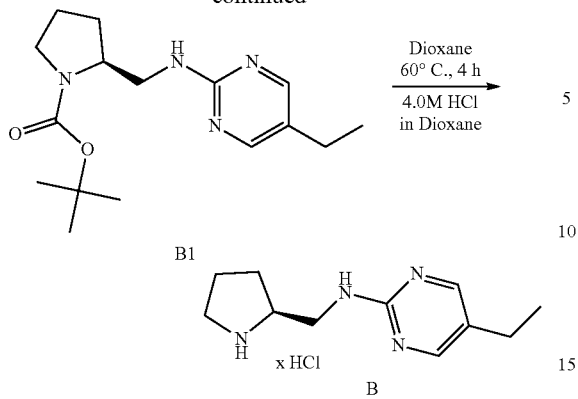

B1

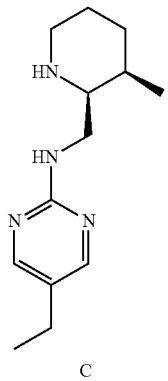

C

Step 1: Synthesis of Compound B1: 2-Chloro-5-ethyl-pyrimidine (0.2 g, 1.37 mmol) and (S)-1-Boc-2-(aminomethyl)-pyrrolidine (0.28 g, 1.37 mmol) were dissolved in dry DMF (5.0 mL). The Cs$_2$CO$_3$ (0.89 g, 2.75 mmol) was added and reaction mixture was stirred at 120° C. temperature for 24 h. TLC shows product formation. The reaction mixture was diluted with water. The product was extracted with ethyl acetate. The combined ethyl acetate layer was washed with water followed by brine. The organic layer was separated and dried over anhydrous sodium sulfate. The evaporation of solvent gave crude product. The crude product was purified by ISCO combi-flash chromatography system, mobile phase: EtOAc:Hexane gradient. The desired liquid product was isolated 0.27 g (yield 64.2%). MS (ESI) mass calcd. for C$_{16}$H$_{26}$N$_4$O$_2$, 306.4; m/z found 307.1 [M+H]$^+$.

Step 2: Synthesis of Intermediate B: The same procedure was used as intermediate A.

3. Synthesis of Intermediate C:

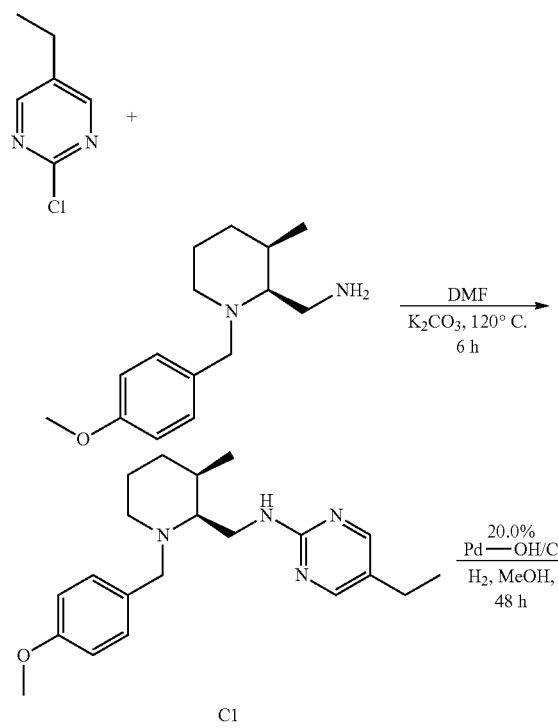

Step 1: Synthesis of Intermediate C1: [(2S,3R)-1-[4-methoxyphenyl)methyl]-3-methylpiperidine-2-yl]methanamine (0.35 g, 1.4 mmol) and 2-chloro-5-ethyl-pyrimidine (0.2 g, 1.4 mmol) were dissolved in dry DMF (4.0 mL). The K$_2$CO$_3$ (0.39 g, 2.82 mmol) was added and reaction mixture was stirred at 120° C. temperature for 6 h. TLC shows product formation. The reaction mixture was diluted with water. The product was extracted with ethyl acetate. The combined ethyl acetate layer was washed with water followed by brine. The organic layer was separated and dried over anhydrous sodium sulfate. The evaporation of solvent gave crude product. The crude product was purified by Combiflash chromatography system, mobile phase: EtOAc: Hexane, gradient. The 0.33 g of product was obtained (yield 65.4%). MS (ESI) mass calcd. for C$_{21}$H$_{30}$N$_4$O, 354.5; m/z found 355.2 [M+H]$^+$, $^1$H NMR (400 MHz, CHLOROFORM-d) δ ppm 0.85-0.94 (d, J=8.0 Hz, 3H) 1.16 (t, J=8.0 Hz, 3H) 1.25-1.47 (m, 2H) 1.50-1.84 (m, 2H) 2.05-2.25 (m, 1H) 2.35-2.47 (q, J=8.0 Hz, 2H) 2.47-2.60 (m, 1H) 2.62-2.83 (m, 2H) 3.33-3.46 (m, 2H) 3.77 (s, 3H) 3.78-3.85 (m, 2H) 5.68 (br s, 1H) 6.84 (d, J=8.66 Hz, 2H) 7.24-7.31 (m, 2H) 8.12 (s, 2H).

Step 2: Synthesis of Intermediate C: Compound C1 (0.1 g, 0.3 mmol) was dissolved in MeOH (3.0 mL). The 20.0% Pd—OH/C (30.0 mg) was added and reaction mixture was stirred at ambient temperature for 24 h. The TLC shows little amount of starting material and product formation. The 20.0% Pd—OH/C (30.0 mg) was further added and reaction mixture was stirred at ambient temperature for another 24 h. The TLC shows completion of reaction. The LCMS data shows m/z 235 of product formation. The reaction mixture was filtered over celite and washed with MeOH. The filtrate was evaporated under reduced pressure to obtain 66.0 mg of crude product. The crude product is used in next step without purification. MS (ESI) mass calcd. for C$_{13}$H$_{22}$N$_4$, 234.3; m/z found 235.2 [M+H]$^+$.

4. Synthesis of Intermediate D:

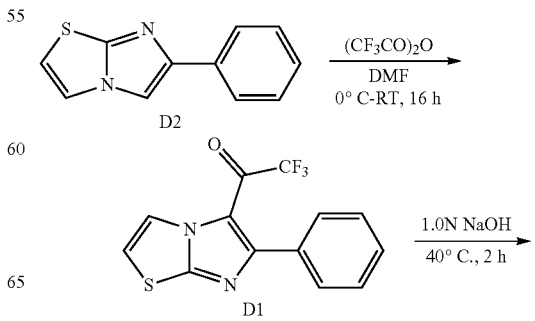

-continued

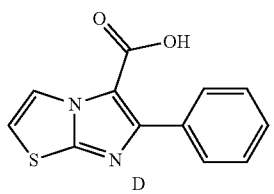

D

Step 1: Synthesis of Compound D1: Compound D2 (prepared according to Meakins, G. et al., Journal of the Chemical Society, Perkin Transactions 1, 1989, 3, p. 643-648) (0.5 g, 2.5 mmol) was dissolved in dry DMF (3.0 mL). The trifluoroacetic acid anhydride (1.73 mL, 12.45 mmol) was added at 0° C. temperature and reaction was allowed to warm at ambient temperature for 16 h. LCMS data shows product formation m/z 296.9. The reaction mixture was diluted with water and basified by saturated solution of $NaHCO_3$. The solid ppts were filtered and vacuum dried to yield 0.71 g of solid product (yield 96.8%). MS (ESI) mass calcd. for $C_{13}H_8F_3N_2OS$, 296.3; m/z found 296.9 $[M+H]^+$.

Step 2: Synthesis of Compound D: Compound D1 (0.1 g, 0.34 mmol) was dissolved in MeOH (3.0 mL). The 1.0 N aq. NaOH solution (1.7 mL, 1.7 mmol) was added and reaction mixture was stirred at room temperature for 16 h. LCMS data shows starting material. The reaction mixture was heated at 40° C. temperature for 4 h. LCMS shows product formation m/z 245. The reaction mixture was concentrated under reduced pressure and acidified with 1.0 M aq. HCl solution. The solid ppts were collected and dried in oven overnight to provide 67.6 mg, (yield 82.1%). MS (ESI) mass calcd. for $C_{12}H_8N_2O_2S$, 244.3; m/z found 245.0 $[M+H]^+$.

5. Synthesis of Intermediate E:

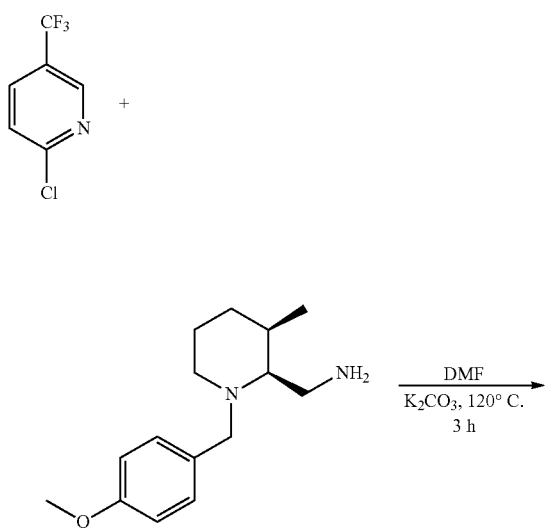

-continued

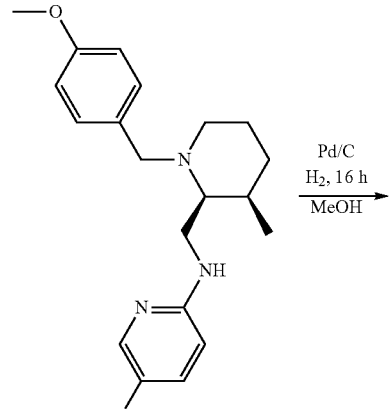

E1

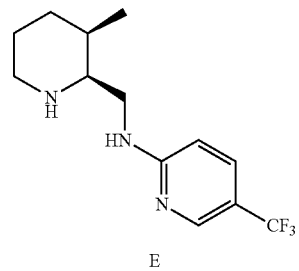

E

Step 1: Synthesis of Compound E1: [(2S,3R)-1-[4-Methoxyphenyl)methyl]-3-methylpiperidine-2-yl]methanamine (0.32 g, 1.29 mmol) and 2-chloro-5-trifluoromethyl-pyridine (0.23 g, 1.29 mmol) were dissolved in dry DMF (5.0 mL). The $K_2CO_3$ (0.36 g, 2.58 mmol) was added and reaction mixture was stirred at 120° C. temperature for 4 h. TLC shows product formation and LCMS shows m/z 394 of product formation. The reaction mixture was diluted with water. The product was extracted with ethyl acetate. The combined ethyl acetate layer was washed with water followed by brine. The organic layer was separated and dried over anhydrous sodium sulfate. Evaporation of solvent gave crude product. The crude product was purified by ISCO combiflash chromatography system, mobile phase: DCM:MeOH (90:10 v/v mL). The product band was isolated. Pure 0.41 g of the product was obtained with m/z 394 (yield 81.4%). MS (ESI) mass calcd. For $C_{21}H_{26}F_3N_3O$, 393.5; m/z found 394.1 $[M+H]^+$, $^1H$ NMR (400 MHz, CHLOROFORM-d) δ ppm 0.88 (d, J=7.04 Hz, 3H) 1.19-1.46 (m, 2H) 1.54-1.65 (m, 1H) 1.65-1.83 (m, 1H) 2.07-2.22 (m, 1H) 2.50-2.65 (m, 1H) 2.65-2.80 (m, 2H) 3.20-3.38 (m, 2H) 3.78 (s, 3H) 3.79-3.84 (m, 2H) 5.67 (br s, 1H) 6.32 (d, J=8.80 Hz, 1H) 6.80-6.89 (m, 2H) 7.15-7.29 (m, 2H) 7.49 (dd, J=8.80, 2.35 Hz, 1H) 8.28-8.32 (m, 1H).

Step 2: Synthesis of Intermediate E: Compound E1 (0.02 g, 0.5 mmol) was dissolved in MeOH (5.0 mL). The 10.0% Pd/C (60.0 mg) was added and reaction mixture was stirred at ambient temperature for 24 h under $H_2$ atm. The TLC shows completion of reaction. The LCMS data shows m/z 274 of product formation. The reaction mixture was filtered over celite and washed with MeOH. The filtrate was evaporated under reduced pressure to obtain 0.16 g of crude product. MS (ESI) mass calcd. for $C_{13}H_{18}F_3N_3$, 273.3; m/z found 274.1 $[M+H]^+$.

6. Synthesis of Intermediate F:

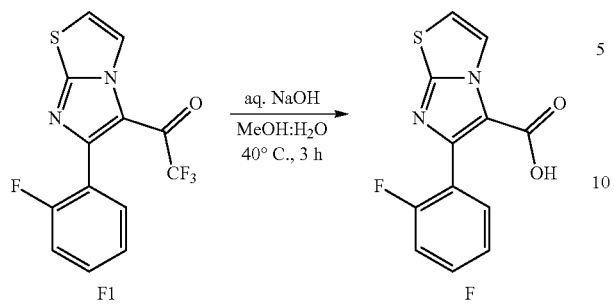

Step 1: Synthesis of Intermediate F: Compound F₁ (prepared using similar procedure used for synthesis of compound D1 above) (0.05 g, 0.16 mmol) was dissolved in Methanol:water (2.0 mL, 3:1). The NaOH (0.07 g, 1.8 mmol) was added and the reaction mixture was stirred at 40° C. temperature for 3 h. LCMS shows desired product formation m/z 263. The reaction mixture was concentrated under reduced pressure and dissolved in water. The aqueous layer was acidified with 1.0 M HCl solution (PH=3.0). The ppts were filtered and afforded 0.027 g of solid (yield 65.0%). MS (ESI) mass calcd. for $C_{12}H_7FN_2O_2S$, 262.3; m/z found 262.9 [M+H]⁺.

7. Synthesis of Intermediate G:

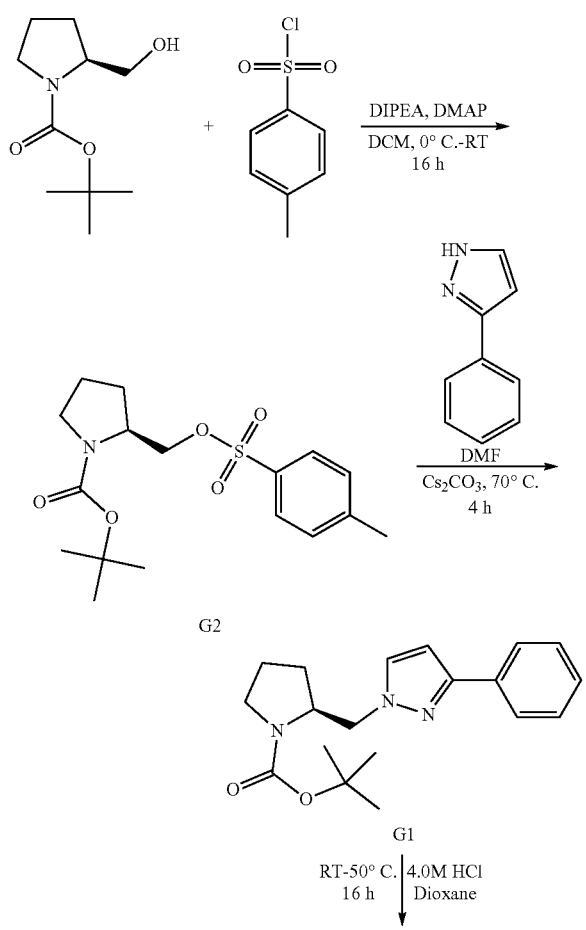

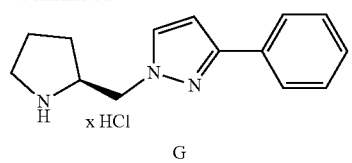

Step 1: Synthesis of Compound G2: The N-Boc-L-Prolinol (0.5 g, 2.48 mmol) was dissolved in DCM (10.0 mL). The DIPEA (0.9 mL, 4.97 mmol) was added followed by DMAP (0.61 g, 4.97 mmol). The reaction mixture was cooled in ice bath and p-TsCl (0.52 g, 2.73 mmol) was added. The reaction mixture was stirred and gradually warmed to room temperature for 16 h. The LCMS shows product formation m/z 256, 300. The reaction mixture was diluted with water. The product was extracted with DCM. The DCM layer was separated and dried over anhydrous Na₂SO₄. The evaporation of solvent gave 0.88 g of product (yield Quant.). MS (ESI) mass calcd. for $C_{17}H_{25}NO_5S$, 355.5; m/z found 300.1, 256.1 [M+H]⁺

Step 2: Synthesis of Compound G1: Compound G1 (0.88 g, 2.48 mmol) and 3-phenyl-1H-pyrazole (0.43 g, 2.98 mmol) were dissolved in dry DMF (5.0 mL). The Cs₂CO₃ (1.61 g, 4.96 mmol) was added and the reaction mixture was stirred at 70° C. temperature for 4 h. The LCMS shows product formation m/z 328. The reaction mixture was cooled to ambient temperature and diluted with water. The product was extracted with ethyl acetate. The EtOAc layer was separated and dried over anhydrous Na₂SO₄. The evaporation of solvent gave crude product. The crude product was purified by column chromatography, mobile phase: EtOAc: Hexane gradient, afforded 0.73 g of pure product (yield 89.5%). MS (ESI) mass calcd. for $C_{19}H_{25}N_3O_2$, 327.4; m/z found 328.3 [M+H]⁺.

Step 3: Synthesis of Intermediate G: Compound G1 (0.73 g, 2.24 mmol) was dissolved in dry dioxane (10.0 mL). The 4.0 M HCl solution in dioxane (2.8 mL, 11.2 mmol) was added and reaction mixture was stirred at 50° C. temperature for 16 h. LCMS shows product formation m/z 228. The reaction mixture was filtered and washed with hexane (5.0 mL×3) to obtain the 0.53 g of solid product (yield Quant.). MS (ESI) mass calcd. for $C_{14}H_{17}N_3$, 227.1; m/z found 228.2 [M+H]⁺, ¹H NMR (400 MHz, CHLOROFORM-d) δ ppm 1.74-1.94 (m, 1H) 1.94-2.05 (m, 1H) 2.06-2.15 (m, 1H) 2.16-2.35 (m, 1H) 3.21-3.45 (m, 2H) 4.33 (br s, 1H) 4.86 (dd, J=14.82, 3.96 Hz, 1H) 5.07 (br dd, J=14.67, 8.66 Hz, 1H) 6.75 (d, J=2.20 Hz, 1H) 7.34-7.48 (m, 3H) 7.76-7.87 (m, 2H) 8.44 (d, J=2.49 Hz, 1H) 9.51-10.12 (br, 1H).

8. Synthesis of Intermediate H:

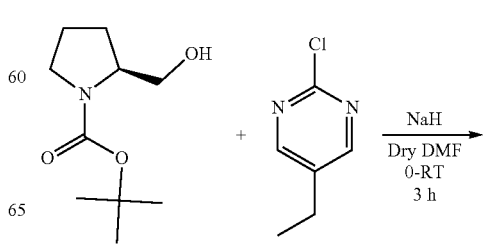

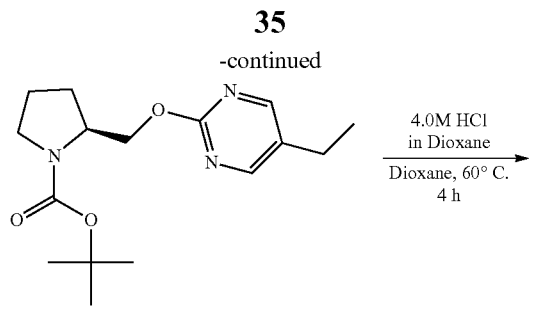

H1

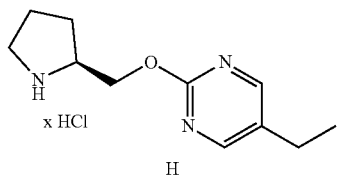

H

Step 1: Synthesis of Compound H$_1$: N-Boc-L-Prolinol (0.2 g, 0.99 mmol) was dissolved in dry DMF (4.0 mL). The NaH (0.08 g, 2.0 mmol) was added under ice cooling. The 2-chloro-5-ethyl-pyrimidine (0.2 g, 1.5 mmol) was added under cooling and reaction mixture was gradually warmed at room temperature under stirring for 3 h. The LCMS shows product formation m/z 308.2. The reaction mixture was diluted with water. The product was extracted with ethyl acetate three times. The EtOAc layers were separated and dried over anhydrous Na$_2$SO$_4$. The evaporation of solvent gave crude product. The crude product was purified by column chromatography, mobile phase: EtOAc:Hexane gradient. The 0.3 g of pure product was obtained (yield Quantitative). MS (ESI) mass calcd. for C$_{16}$H$_{26}$N$_3$O$_3$, 307.4; m/z found 308.2 [M+H]$^+$.

Step 2: Synthesis of Intermediate H: Compound H$_1$ (0.3 g, 0.99 mmol) were dissolved in dry dioxane (4.0 mL). The 4.0 M HCl solution in dioxane (2.48 mL, 9.9 mmol) was added and reaction mixture was stirred at 60° C. temperature for 4 h. LCMS shows product formation m/z 208.1. The reaction mixture was concentrated under reduced pressure to obtain 0.32 g of liquid product. MS (ESI) mass calcd. for C$_{11}$H$_{17}$N$_3$O, 207.3; m/z found 208.1 [M+H]$^+$.

9. Synthesis of Intermediate I:

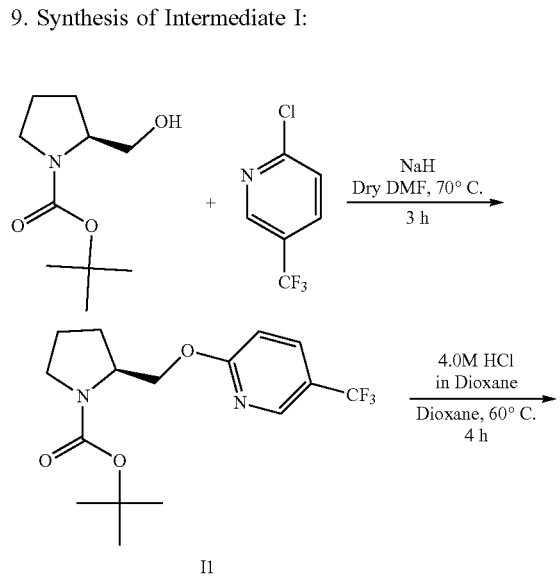

I1

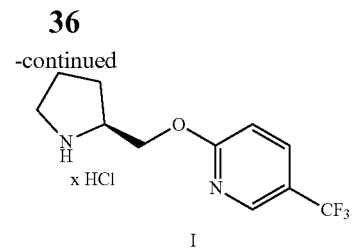

I

Step 1: Synthesis of Compound I1: N-Boc-L-Prolinol (0.2 g, 0.99 mmol) was dissolved in dry DMF (4.0 mL). The NaH (0.08 g, 2.0 mmol) was added followed by 2-Chloro-5-trifluoromethylpyridine (0.27 g, 1.5 mmol). The reaction mixture was heated at 70° C. temperature for 3 h. The LCMS shows product formation m/z 347.1. The reaction mixture was diluted with water. The product was extracted with ethyl acetate three times. The EtOAc layers were separated and dried over anhydrous Na$_2$SO$_4$. The evaporation of solvent gave crude product. The crude product was purified by column chromatography, mobile phase: EtOAc: Hexane gradient. The 0.3 g of pure product was obtained (yield 86.0%). MS (ESI) mass calcd. for C$_{16}$H$_{21}$F$_3$N$_2$O$_3$, 346.3; m/z found 347.1 [M+H]$^+$.

Step 2: Synthesis of Intermediate I: Compound I1 (0.3 g, 0.86 mmol) was dissolved in dry dioxane (2.0 mL). The 4.0 M HCl solution in dioxane (2.14 mL, 8.6 mmol) was added and reaction mixture was stirred at 60° C. temperature for 4 h. LCMS shows product formation m/z 247.1. The reaction mixture was filtered and washed with hexane (5.0 mL×3) to obtain the 0.27 g of solid product (yield Quant.). MS (ESI) mass calcd. for C$_{11}$H$_{13}$F$_3$N$_2$O, 246.2; m/z found 247.1 [M+H]$^+$, $^1$H NMR (400 MHz, CHLOROFORM-d) δ ppm 1.87-1.99 (m, 1H) 1.99-2.08 (m, 1H) 2.08-2.17 (m, 1H) 2.17-2.29 (m, 1H) 3.32-3.49 (m, 2H) 3.96-4.09 (m, 1H) 4.60-4.77 (m, 2H) 7.00 (d, J=8.73 Hz, 1H) 7.77 (dd, J=8.73, 2.35 Hz, 1H) 8.37-8.42 (m, 1H) 9.74 (br s, 1H) 10.32 (br s, 1H).

10. Synthesis of Intermediate K or I: Procedure was Used as Described in European Journal of Medicinal Chemistry 1995 Vol. 30 #11 p. 901-909.

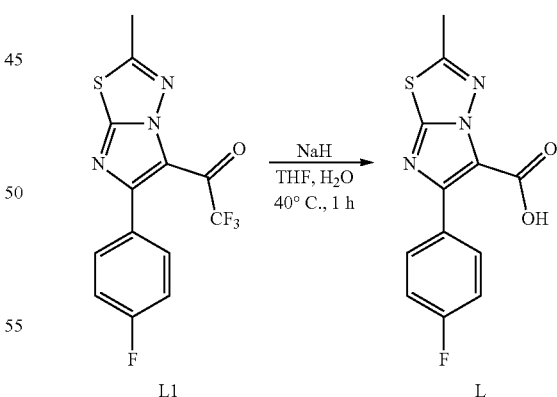

L1                               L

Synthesis of Intermediate L: Compound L1 (prepared using the same procedures used for synthesis of compound D2 & D1 above) (0.2 g, 0.61 mmol) was dissolved in THF (4.0 mL). The NaH (0.12 g, 3.0 mmol) was added and reaction mixture was stirred at room temperature. The water (0.04 mL) was added at room temperature and reaction mixture was heated at 40° C. for 1 h. LCMS shows desired product formation m/z 278 and decarboxylated product formation in (1:1 ratio). The reaction mixture was concentrated under reduced pressure and dissolved in 10.0 mL of water. The undesired product was extracted with ethyl acetate. The aq. Layer was separated and acidified with 1.0 M HCl solution (PH=4.0). The ppts were filtered and collected. The drying afforded 0.11 g of product (yield 65.3%). MS (ESI) mass calcd. for $C_{12}H_8FN_3O_2S$, 277.3; m/z found 278.0 $[M+H]^+$.

11. Synthesis of Intermediate M:

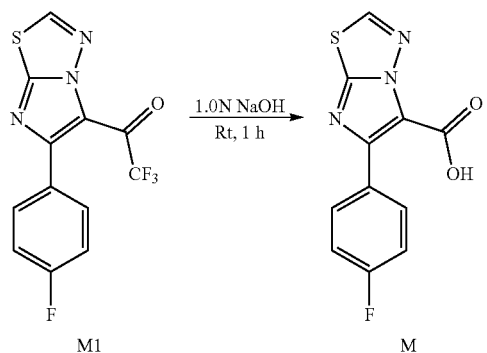

Synthesis of Intermediate M: Compound M1 (prepared using the same procedures used for synthesis of compound D2 & D1 above) (0.1 g, 0.3 mmol) was diluted with 1.0 N aq. NaOH solution (1.6 mL, 1.6 mmol) and reaction mixture was stirred at room temperature for 1 h. LCMS shows some amount of desired product formation along with undesired decarboxylated side product. The reaction mixture was concentrated under reduced pressure and dissolved in 10.0 mL of water. The undesired product was extracted with ethyl acetate. The aq. Layer was separated and acidified with 1.0 M HCl solution (PH=3.0). The aq. Layer was concentrated and ppts were filtered and collected. The ppt shows desired product m/z 264 and unknown products. (~20.0 mg of crude product obtained). MS (ESI) mass calcd. for $C_{11}H_6FN_3O_2S$, 263.3; m/z found 264.0 $[M+H]^+$.

II. Synthesis of Example Compounds

A. Example 1

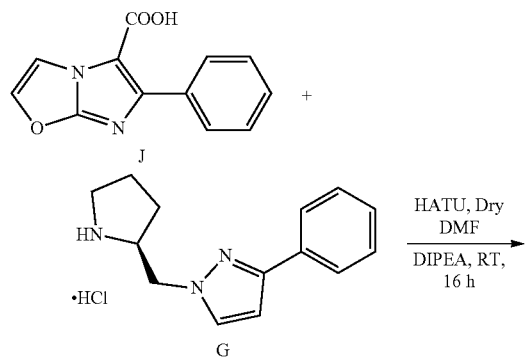

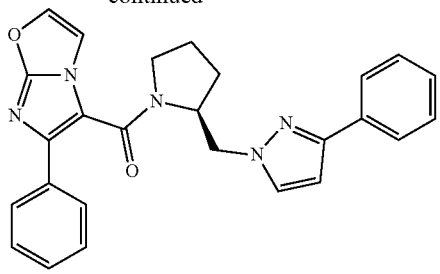

Example 1

Synthesis of Compound Example 1: Compound J (prepared using the same procedures used for synthesis of compound D1 using 2-phenylimidazo[2,1-b]oxazole) above (0.025 g, 0.11 mmol) was dissolved in dry DMF (1.5 mL). The HATU (0.06 g, 0.16 mmol) was added followed by DIPEA (0.19 mL, 1.1 mmol). Compound G (0.029 g, 0.11 mmol) was added and reaction mixture was stirred at ambient temperature for 16 h. LCMS data shows product formation m/z 438.1. The reaction mixture was diluted with saturated solution of $NaHCO_3$. The product was extracted with ethyl acetate. The combined ethyl acetate layer was washed with water followed by brine. The organic layer was separated and dried over anhydrous sodium sulfate. Evaporation of solvent gave crude product. The crude product was purified by prep-TLC plate, mobile phase: EtOAc:Hexane (60:40 v/v mL). The desired product band was isolated, affording 37.4 mg of pure product (yield 78.7%). MS (ESI) mass calcd. for $C_{26}H_{23}N_5O_2$, 437.5; m/z found 438.1 $[M+H]^+$, $^1H$ NMR (400 MHz, CHLOROFORM-d) δ ppm 1.51 (br s, 2H) 1.80-2.12 (m, 2H) 2.35-2.62 (m, 1H) 3.14 (br s, 1H) 3.51-4.20 (m, 1H) 4.55 (br s, 2H) 6.60 (br s, 1H) 7.21-7.33 (m, 4H) 7.33-7.46 (m, 3H) 7.49-7.63 (m, 3H) 7.67 (br s, 1H) 7.73-7.87 (m, 2H).

B. Example 2

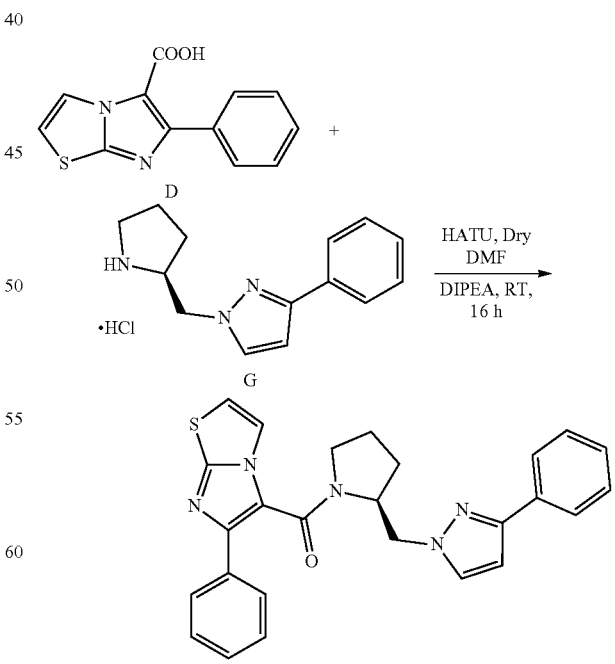

Example 2

Synthesis of Compound Example 2: Compound D (0.025 g, 0.11 mmol) was dissolved in dry DMF (1.5 mL). The HATU (0.06 g, 0.15 mmol) was added followed by DIPEA (0.18 mL, 1.0 mmol). Compound G (0.027 g, 0.1 mmol) was added and reaction mixture was stirred at ambient temperature for 16 h. LCMS data shows product formation m/z 454.1. The reaction mixture was diluted with saturated solution of NaHCO$_3$. The product was extracted with ethyl acetate. The combined ethyl acetate layer was washed with water followed by brine. The organic layer was separated and dried over anhydrous sodium sulfate. The evaporation of solvent gave crude product. The crude product was purified by prep-TLC plate, mobile phase: EtOAc:Hexane (60:40 v/v mL). The desired product band was isolated affording 35.8 mg of pure product (yield 77.7%). MS (ESI) mass calcd. for C$_{26}$H$_{23}$N$_5$OS, 453.6; m/z found 454.1 [M+H]$^+$, $^1$H NMR (400 MHz, CHLOROFORM-d) δ ppm 1.43-1.65 (m, 2H) 1.80-2.17 (m, 2H) 2.53 (br d, J=9.39 Hz, 1H) 3.09-3.20 (m, 1H) 3.78 (br s, 1H) 4.57 (br s, 2H) 6.59 (br s, 1H) 6.79-6.88 (m, 1H) 7.24-7.44 (m, 6H) 7.46-7.58 (s, 1H) 7.62 (dd, J=8.07, 1.32 Hz, 2H) 7.68-7.83 (d, J=4.0 Hz, 2H) 7.84-7.96 (m, 1H).

C. Example 3

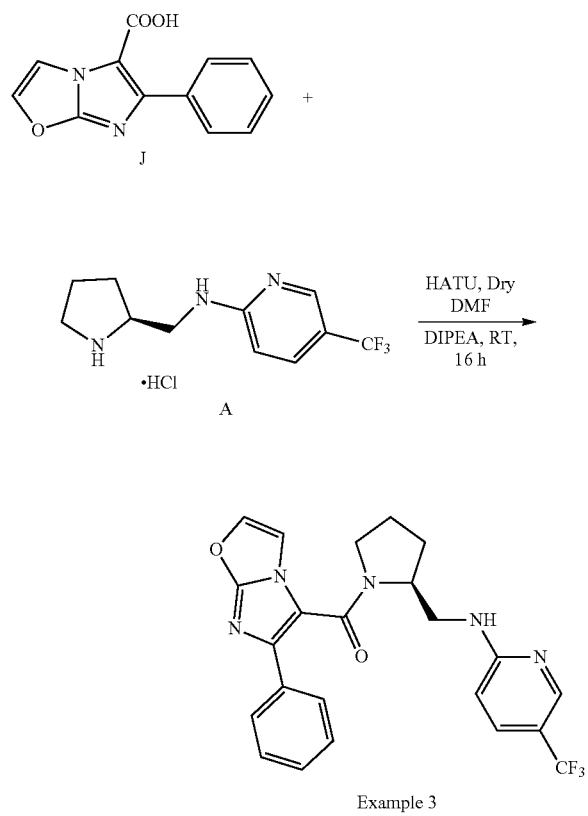

Example 3

Synthesis of Compound Example 3: Compound J (0.025 g, 0.11 mmol) was dissolved in dry DMF (1.5 mL). The HATU (0.06 g, 0.16 mmol) was added followed by DIPEA (0.19 mL, 1.1 mmol). Compound A (0.038 g, 0.11 mmol) was added and reaction mixture was stirred at ambient temperature for 16 h. LCMS data shows product formation m/z 456.1. The reaction mixture was diluted with saturated solution of NaHCO$_3$. The product was extracted with ethyl acetate. The combined ethyl acetate layer was washed with water followed by brine. The organic layer was separated and dried over anhydrous sodium sulfate. The evaporation of solvent gave crude product. The crude product was purified by prep-TLC plate, mobile phase: EtOAc:Hexane (50:50 up to 70:30 v/v mL). The desired product band was isolated affording 29.0 mg of pure product (yield 58.6%). MS (ESI) mass calcd. for C$_{23}$H$_{20}$F$_3$N$_5$O$_2$, 455.4; m/z found 456.1 [M+H]$^+$, $^1$H NMR (400 MHz, CHLOROFORM-d) δ ppm 1.42-1.77 (m, 2H) 1.78-1.98 (br s, 1H) 2.09-2.30 (br s, 1H) 2.54 (br s, 1H) 3.31 (br s, 1H) 3.56 (br s, 2H) 4.67 (br s, 1H) 6.25 (br s, 1H) 6.54 (br d, J=6.53 Hz, 1H) 7.27-7.34 (m, 3H) 7.43 (s, 1H) 7.48-7.65 (m, 4H) 8.33 (br s, 1H).

D. Example 4

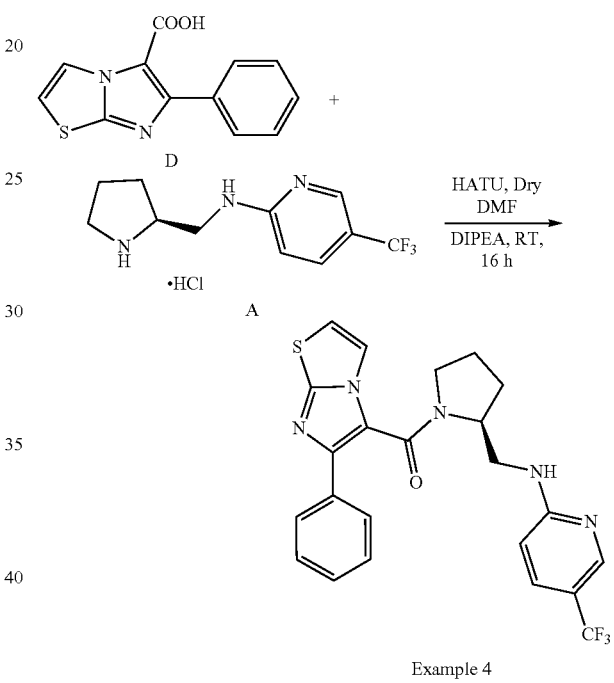

Example 4

Synthesis of Compound Example 4: Compound D (0.019 g, 0.077 mmol) was dissolved in dry DMF (1.5 mL). The HATU (0.044 g, 0.12 mmol) was added followed by DIPEA (0.13 mL, 0.77 mmol). Compound A (0.027 g, 0.077 mmol) was added and reaction mixture was stirred at ambient temperature for 16 h. LCMS data shows product formation m/z 472.1. The reaction mixture was diluted with saturated solution of NaHCO$_3$. The product was extracted with ethyl acetate. The combined ethyl acetate layer was washed with water followed by brine. The organic layer was separated and dried over anhydrous sodium sulfate. The evaporation of solvent gave crude product. The crude product was purified by prep-TLC plate, mobile phase: EtOAc:Hexane (50:50 up to 70:30 v/v mL). The desired product band was isolated affording 24.4 mg of pure product (yield 67.1%). MS (ESI) mass calcd. for C$_{23}$H$_{20}$F$_3$N$_5$OS, 471.5; m/z found 472.1 [M+H]$^+$, $^1$H NMR (400 MHz, CHLOROFORM-d) δ ppm 1.40-1.75 (m, 2H) 1.75-1.98 (m, 1H) 2.00-2.00-2.26 (m, 1H). 2.36-2.68 (m, 1H) 3.18-3.41 (m, 1H) 3.43-3.78 (m, 2H) 4.71 (br s, 1H) 6.13-6.44 (m, 1H) 6.55 (br d, J=8.44 Hz, 1H) 6.90 (br d, J=3.67 Hz, 1H) 7.26-7.43 (m, 3H) 7.43-7.64 (m, 3H) 7.79 (br d, J=3.67 Hz, 1H) 8.34 (br s, 1H).

E. Example 5

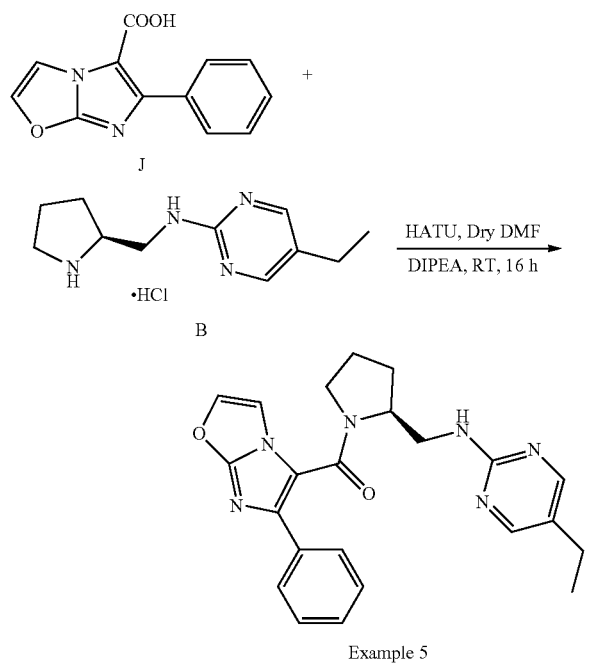

Example 5

Synthesis of Compound Example 5: Compound J (0.025 g, 0.11 mmol) was dissolved in dry DMF (1.5 mL). The HATU (0.06 g, 0.16 mmol) was added followed by DIPEA (0.19 mL, 1.1 mmol). Compound B (0.038 g, 0.11 mmol) was added and reaction mixture was stirred at ambient temperature for 16 h. LCMS data shows product formation m/z 417.1. The reaction mixture was diluted with saturated solution of NaHCO$_3$. The product was extracted with ethyl acetate. The combined ethyl acetate layer was washed with water followed by brine. The organic layer was separated and dried over anhydrous sodium sulfate. The evaporation of solvent gave crude product. The crude product was purified by prep-TLC plate, mobile phase: EtOAc and then DCM: MeOH (95:05 v/v mL). The desired product band was isolated affording 34.5 mg of pure product (yield 76.3%). MS (ESI) mass calcd. for C$_{23}$H$_{24}$N$_6$O$_2$, 416.5; m/z found 417.1 [M+H]$^+$, $^1$H NMR (400 MHz, CHLOROFORM-d) δ ppm 1.04-1.30 (m, 3H) 1.31-1.72 (m, 2H) 1.75-2.2 (m, 2H) 2.37-2.48 (m, 2H) 2.48-2.93 (m, 1H) 2.94-3.52 (m, 1H) 3.53-3.82 (m, 2H) 3.91-4.8 (m, 1H) 5.2-6.21 (m, 1H) 7.20-7.37 (m, 3H) 7.38-7.6 (m, 3H) 7.64 (br s, 1H) 7.72-8.27 (m, 2H).

F. Example 6

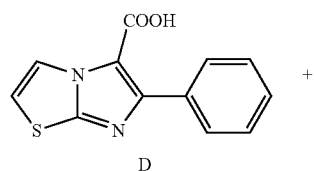

D

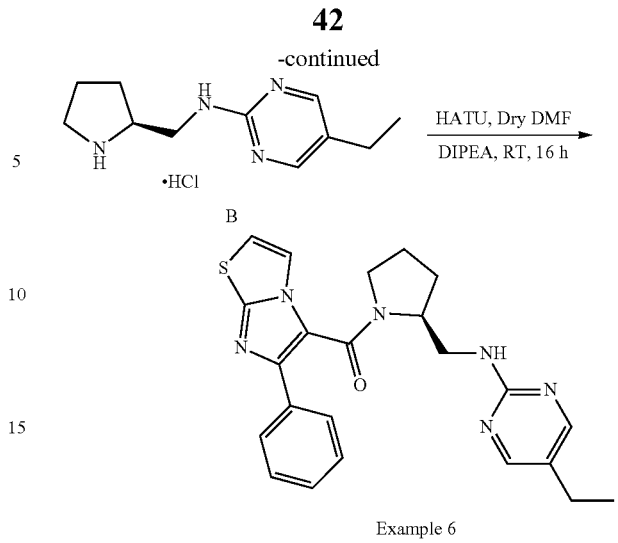

Example 6

G. Synthesis of Compound Example 6: Compound D (0.025 g, 0.11 mmol) was dissolved in dry DMF (1.5 mL). The HATU (0.06 g, 0.15 mmol) was added followed by DIPEA (0.18 mL, 1.0 mmol). Compound B (0.036 g, 0.1 mmol) was added and reaction mixture was stirred at ambient temperature for 16 h. LCMS data shows product formation m/z 433. The reaction mixture was diluted with saturated solution of NaHCO$_3$. The product was extracted with ethyl acetate. The combined ethyl acetate layer was washed with water followed by brine. The organic layer was separated and dried over anhydrous sodium sulfate. The evaporation of solvent gave crude product. The crude product was purified by prep-TLC plate, mobile phase: DCM: MeOH (97:03 v/v mL). The desired product band was isolated affording 23.0 mg of product was obtained (yield 52.3%). MS (ESI) mass calcd. for C$_{23}$H$_{24}$N$_6$OS, 432.5; m/z found 433.1 [M+H]$^+$, $^1$H NMR (400 MHz, CHLOROFORM-d) δ ppm 1.11-1.25 (m, 3H) 1.46-1.72 (m, 2H) 1.75-2.2 (m, 2H) 2.38-2.48 (m, 2H) 2.48-2.87 (m, 1H) 3.0-3.55 (m, 1H) 3.55-3.83 (m, 2H) 3.91-5.15 (m, 1H) 5.84-6.18 (m, 1H) 6.68-6.93 (m, 1H) 7.26-7.44 (m, 3H) 7.44-7.69 (m, 3H) 7.72-7.96 (m, 1H) 8.03-8.22 (m, 1H).

Example 7

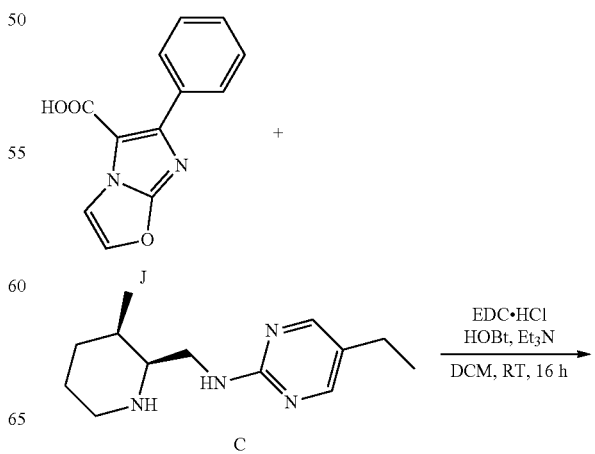

43

-continued

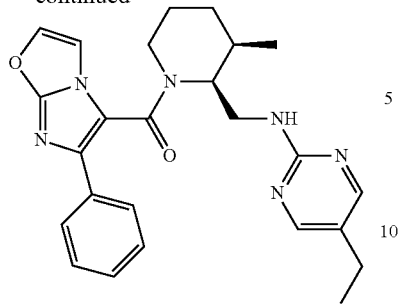

Example 7

Synthesis of Compound Example 7: Compound J (0.025 g, 0.11 mmol) was dissolved in dry DCM (2.0 mL). The EDC·HCl (0.042 g, 0.22 mmol) and HOBt (0.029 g, 0.22 mmol) were added followed by Et$_3$N (0.08 mL, 0.54 mmol). Compound C (0.025 g, 0.11 mmol) was dissolved in dry DCM (1.0 mL) and added to the reaction mixture. The reaction mixture was stirred at ambient temperature for 16 h. LCMS data shows product formation m/z 445. The reaction mixture was concentrated and diluted with saturated solution of NaHCO$_3$. The product was extracted with ethyl acetate. The combined ethyl acetate layer was washed with water followed by brine. The organic layer was separated and dried over anhydrous sodium sulfate. The evaporation of solvent gave crude product. The crude product was purified by prep-TLC plate, mobile phase: DCM:MeOH (97:03 v/v mL). The desired product band was isolated to obtain 21.0 mg of product (yield 43.5%). MS (ESI) mass calcd. for C$_{25}$H$_{28}$N$_6$O$_2$, 444.5; m/z found 445.2 [M+H]$^+$, $^1$H NMR (400 MHz, CHLOROFORM-d) δ ppm 0.49 (br d, J=8.0 Hz, 2H) 0.99-1.06 (d, J=8.0 Hz, 1H) 1.09-1.23 (t, 3H) 1.25-1.53 (m, 3H) 1.65-2.10 (m, 2H) 2.30-2.47 (m, 2H) 2.64-2.86 (m, 1H) 3.11-3.34 (m, 2H) 3.35-3.90 (m, 1H) 4.11-4.47 (m, 1H) 4.93-5.72 (m, 1H) 7.17-7.29 (m, 1H) 7.29-7.42 (m, 3H) 7.48-7.67 (m, 3H) 7.85 (br s, 1H) 8.10 (br s, 1H).

G. Example 8

44

-continued

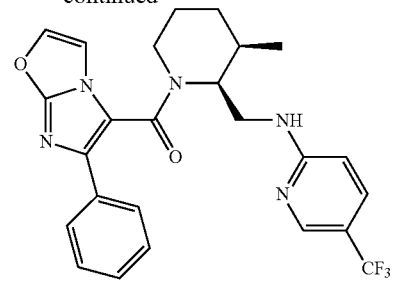

Example 8

Synthesis of Compound Example 8: Compound J (0.025 g, 0.11 mmol) was dissolved in dry DCM (2.0 mL). The EDC·HCl (0.04 g, 0.22 mmol) and HOBt (0.029 g, 0.22 mmol) were added followed by Et$_3$N (0.15 mL, 1.1 mmol). Compound E (0.03 g, 0.11 mmol) was dissolved in dry DCM (2.0 mL) and added to the reaction mixture. The reaction mixture was stirred at ambient temperature for 16 h. LCMS data shows product formation m/z 483. The reaction mixture was concentrated and diluted with saturated solution of NaHCO$_3$. The product was extracted with ethyl acetate. The combined ethyl acetate layer was washed with water followed by brine. The organic layer was separated and dried over anhydrous sodium sulfate. The evaporation of solvent gave crude product. The crude product was purified by prep-TLC plate, mobile phase: EtOAc:Hexane (50:50 v/v mL). The desired product band was isolated to obtain 0.025 g of product (yield 48.2%). MS (ESI) mass calcd. for C$_{25}$H$_{24}$F$_3$N$_5$O$_2$, 483.5; m/z found 484.1 [M+H]$^+$, $^1$H NMR (400 MHz, CHLOROFORM-d) δ ppm 0.49 (br d, J=6.53 Hz, 1H) 1.04 (br d, J=6.82 Hz, 2H) 1.14-1.32 (m, 2H) 1.31-1.52 (m, 2H) 1.62-1.97 (m, 1H) 2.74 (br t, J=12.84 Hz, 1H) 3.10-3.67 (m, 2H) 3.73-4.44 (m, 1H) 4.80-5.13 (m, 1H) 5.58-5.76 (m, 1H) 5.81-6.50 (dd, J=8.0 Hz, 1H) 7.11-7.47 (m, 5H) 7.47-7.62 (m, 3H) 7.99-8.38 (s, 1H).

H. Example 9

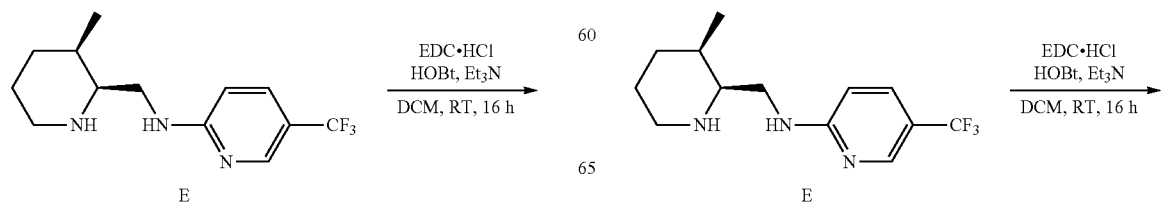

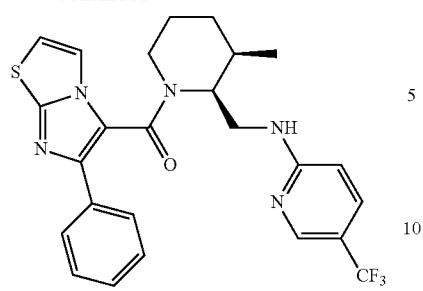

Example 9

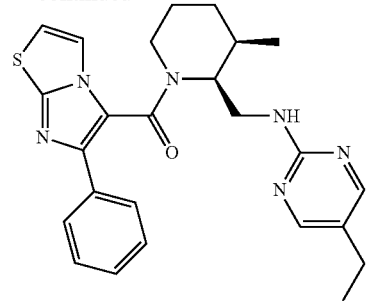

Example 10

Synthesis of Compound Example 9: Compound D (0.025 g, 0.11 mmol) was dissolved in dry DCM (2.0 mL). The EDC·HCl (0.04 g, 0.2 mmol) and HOBt (0.027 g, 0.2 mmol) were added followed by Et$_3$N (0.15 mL, 1.1 mmol). Compound E (0.03 g, 0.1 mmol) was dissolved in dry DCM (2.0 mL) and added to the reaction mixture. The reaction mixture was stirred at ambient temperature for 16 h. LCMS data shows product formation m/z 500. The reaction mixture was concentrated and diluted with saturated solution of NaHCO$_3$. The product was extracted with ethyl acetate. The combined ethyl acetate layer was washed with water followed by brine. The organic layer was separated and dried over anhydrous sodium sulfate. The evaporation of solvent gave crude product. The crude product was purified by prep-TLC plate, mobile phase: EtOAc:Hexane (50:50 v/v mL). The desired product band was isolated to obtain 35.0 mg of desired product (yield 69.0%). MS (ESI) mass calcd. for C$_{25}$H$_{24}$F$_3$N$_5$OS, 499.6; m/z found 500.1 [M+H]$^+$, $^1$H NMR (400 MHz, CHLOROFORM-d) δ ppm 0.51 (d, J=7.04 Hz, 1H) 0.97-1.08 (d, J=4.0 Hz, 2H) 1.08-1.31 (m, 2H) 1.31-1.46 (m, 2H) 1.65-1.99 (m, 1H) 2.76 (br t, J=13.42 Hz, 1H) 3.09-3.63 (m, 2H) 3.77-4.49 (m, 1H) 4.82-5.08 (m, 1H) 5.79 (br d, J=8.73 Hz, 1H) 6.43 (d, J=8.73 Hz, 1H) 6.60-6.91 (dd, J=4.0 Hz, 1H) 7.19-7.44 (m, 3H) 7.48-7.63 (m, 4H) 7.97-8.37 (s, 1H).

Synthesis of Compound Example 10: Compound D (0.025 g, 0.1 mmol) was dissolved in dry DCM (2.0 mL). The EDC·HCl (0.04 g, 0.2 mmol) and HOBt (0.027 g, 0.2 mmol) were added followed by Et$_3$N (0.14 mL, 1.0 mmol). Compound C (0.035 g, 0.15 mmol) was dissolved in dry DCM (1.0 mL) and added to the reaction mixture. The reaction mixture was stirred at ambient temperature for 16 h. LCMS data shows product formation m/z 461. The reaction mixture was concentered and diluted with saturated solution of NaHCO$_3$. The product was extracted with ethyl acetate. The combined ethyl acetate layer was washed with water followed by brine. The organic layer was separated and dried over anhydrous sodium sulfate. The evaporation of solvent gave crude product. The crude product was purified by prep-TLC plate, mobile phase: DCM:MeOH (97:03 v/v mL). The desired band was isolated to obtain 0.018 g of product (yield 38.9%). MS (ESI) mass calcd. for C$_{26}$H$_{28}$N$_6$OS, 460.6; m/z found 461.1 [M+H]$^+$, $^1$H NMR (400 MHz, CHLOROFORM-d) δ ppm 0.51 (d, J=7.12 Hz, 1H) 0.86-1.06 (m, 2H) 1.15 (td, J=7.61, 2.82 Hz, 3H) 1.20-1.62 (m, 2H) 1.64-1.94 (m, 1H) 2.29-2.47 (m, 2H) 2.66-2.86 (m, 1H) 3.06-3.34 (m, 1H) 3.34-3.55 (m, 1H) 3.66-3.90 (m, 2H) 4.12-4.51 (m, 1H) 5.02-5.86 (m, 1H) 6.63-6.72 (d, J=4.0 Hz, 1H) 6.72-6.91 (m, 1H) 7.21-7.44 (m, 3H) 7.50-7.58 (m, 1H) 7.58-7.75 (m, 1H) 7.80 (br s, 1H) 8.10 (d, J=2.79 Hz, 1H).

J. Example 11

I. Example 10

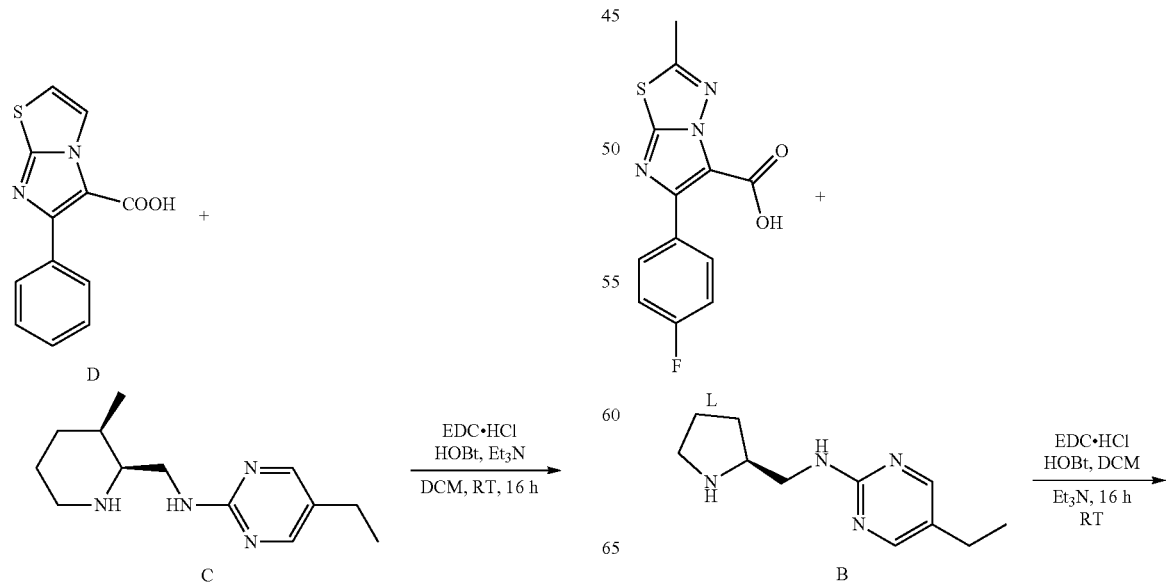

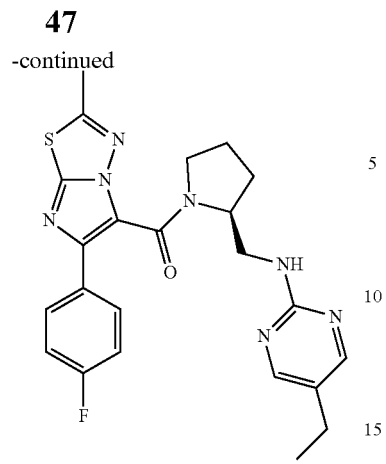

Example 11

Synthesis of Compound Example 11: Compound L (0.025 g, 0.09 mmol) was dissolved in dry DCM (2.0 mL). The EDC·HCl (0.035 g, 0.18 mmol) and HOBt (0.024 g, 0.18 mmol) were added followed by Et$_3$N (0.13 mL, 0.9 mmol). Compound B (0.03 g, 0.09 mmol) was dissolved in dry DCM (2.0 mL) and added to the reaction mixture. The reaction mixture was stirred at ambient temperature for 3 h. LCMS data shows product formation m/z 466. The reaction mixture was diluted with DCM and washed with saturated solution of NaHCO$_3$. The DCM layer was separated and dried over anhydrous Na$_2$SO$_4$. The evaporation of solvent gave crude product. The crude product was purified by prep-TLC plate, mobile phase: EtOAc:MeOH (97.5:2.5 v/v mL). The desired product band was isolated to obtain 0.021 g of product (yield 50.1%). MS (ESI) mass calcd. for C$_{23}$H$_{24}$FN$_7$OS, 465.6; m/z found 466.2 [M+H]$^+$, $^1$H NMR (400 MHz, CHLOROFORM-d) δ ppm 1.13-1.28 (m, 3H) 1.49-1.71 (m, 1H) 1.71-1.81 (m, 1H) 1.86-2.13 (m, 2H) 2.42 (quin, J=7.61 Hz, 2H) 2.84-3.05 (m, 1H) 3.06-3.35 (m, 1H) 3.67-3.83 (m, 2H) 3.89-4.80 (m, 1H) 4.96-6.08 (m, 1H) 6.96-7.07 (m, 2H) 7.49 (br dd, J=8.51, 5.43 Hz, 1H) 7.73 (dd, J=8.66, 5.43 Hz, 1H) 7.86 (s, 1H) 8.12 (s, 1H).

K. Example 12

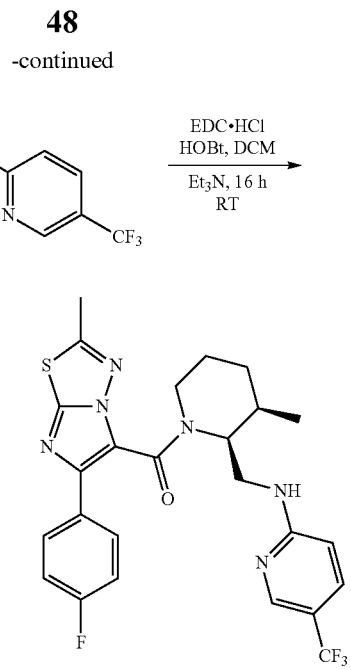

Example 12

Synthesis of Compound Example 12: Compound L (0.02 g, 0.07 mmol) was dissolved in dry DCM (2.0 mL). The EDC·HCl (0.028 g, 0.14 mmol) and HOBt (0.019 g, 0.14 mmol) were added followed by Et$_3$N (0.1 mL, 0.7 mmol). Compound E (0.02 g, 0.07 mmol) was dissolved in dry DCM (2.0 mL) and added to the reaction mixture. The reaction mixture was stirred at ambient temperature for 16 h. LCMS data shows product formation m/z 533. The reaction mixture was diluted with DCM and washed with saturated solution of NaHCO$_3$. The DCM layer was separated and dried over anhydrous Na$_2$SO$_4$. The evaporation of solvent gave crude product. The crude product was purified by prep-TLC plate, mobile phase: EtOAc:Hexane (50:50 v/v mL). The desired product band was isolated to obtain 0.023 g of product (yield 59.1%). MS (ESI) mass calcd. for C$_{26}$H$_{24}$F$_4$N$_6$OS, 532.6; m/z found 533.2 [M+H]$^+$, $^1$H NMR (400 MHz, CHLOROFORM-d) δ ppm 0.58-0.72 (m, 1H) 1.02-1.13 (m, 2H) 1.32-1.64 (m, 2H) 1.67-2.07 (m, 2H) 2.58-2.69 (m, 3H) 2.70-3.06 (m, 1H) 3.14-3.59 (m, 2H) 3.82-4.21 (m, 1H) 4.56-4.93 (m, 1H) 5.15 (br d, J=11.88 Hz, 1H) 5.59 (br s, 1H) 6.46 (br d, J=8.73 Hz, 1H) 6.76-7.02 (br, 1H) 7.10 (br t, J=8.58 Hz, 1H) 7.25-7.56 (m, 1H) 7.56-7.64 (m, 1H) 7.64-7.73 (m, 1H) 8.01-8.40 (m, 1H).

L. Example 13

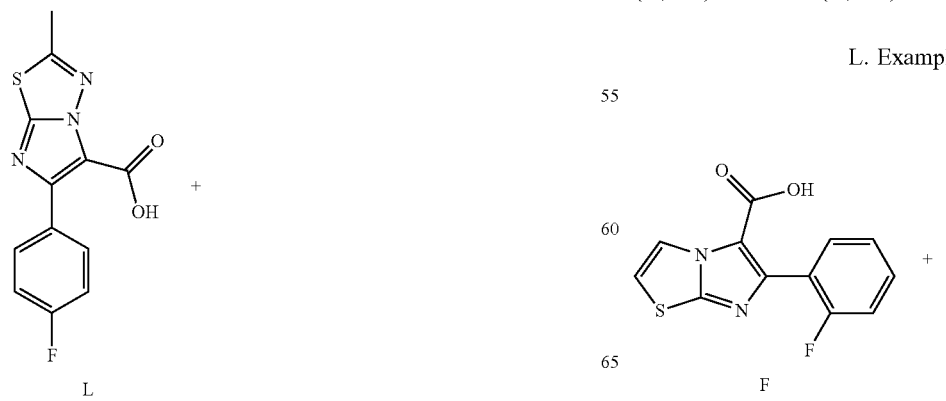

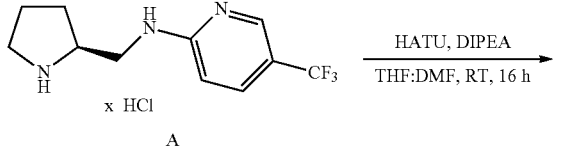

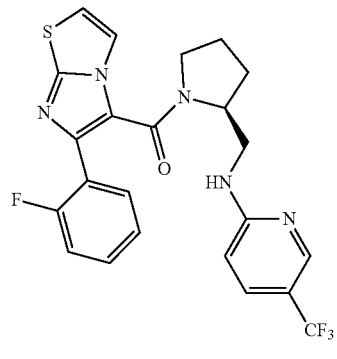

Example 13

Synthesis of Compound Example 13: Compound F (0.025 g, 0.1 mmol) was dissolved in mixture of dry THF:DMF (2.0 mL, 1:1). The HATU (0.036 g, 0.1 mmol) was added followed by DIPEA (0.05 g, 0.4 mmol). Compound A (0.03 g, 0.1 mmol) was added to the reaction mixture. The reaction mixture was stirred at ambient temperature for 16 h. LCMS data shows product formation m/z 490. The reaction mixture was diluted with saturated solution of NaHCO$_3$ and extracted with ethyl acetate. The ethyl acetate layer was separated and dried over anhydrous Na$_2$SO$_4$. The evaporation of solvent gave crude product. The crude product was purified by prep-TLC plate, mobile phase: EtOAc:Hexane (75:25 v/v mL). The desired product band was isolated to obtain 0.015 g of product (yield 31.0%). MS (ESI) mass calcd. for C$_{23}$H$_{19}$F$_4$N$_5$OS, 489.5; m/z found 489.8 [M+H]$^+$, $^1$H NMR (400 MHz, CHLOROFORM-d) b ppm 1.45-1.97 (m, 4H) 2.49 (br s, 1H) 3.35 (br s, 1H) 3.49-3.56 (m, 1H) 3.60 (br s, 1H) 4.62 (br s, 1H) 6.08-6.60 (br s, 1H) 6.92 (br s, 1H) 7.08 (br t, J=9.32 Hz, 1H) 7.15-7.21 (m, 1H) 7.31-7.37 (m, 1H) 7.52 (br d, J=6.97 Hz, 1H) 7.64 (br t, J=7.30 Hz, 1H) 7.75-7.89 (br s, 1H) 7.94-8.02 (s, 1H) 8.31 (br s, 1H).

M. Example 14

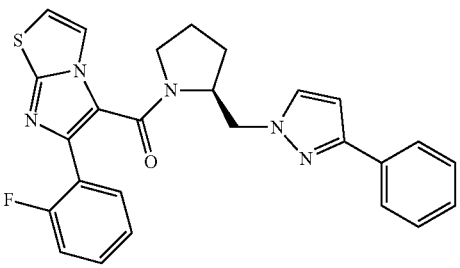

Example 14

Synthesis of Compound Example 14: Compound F (0.03 g, 0.11 mmol) was dissolved in dry THF (2.5 mL). The HATU (0.044 g, 0.11 mmol) was added followed by DIPEA (0.59 g, 0.45 mmol). Compound G (0.029 g, 0.11 mmol) was added to the reaction mixture. The reaction mixture was stirred at ambient temperature for 3 h. LCMS data shows product formation m/z 472. The reaction mixture was diluted with saturated solution of NaHCO$_3$ and extracted with ethyl acetate. The ethyl acetate layer was separated and dried over anhydrous Na$_2$SO$_4$. The evaporation of solvent gave crude product. The crude product was purified by prep-TLC plate, mobile phase: EtOAc:Hexane (30:70 v/v mL). The desired product band was isolated to obtain 0.04 g of product (yield 74.0%). MS (ESI) mass calcd. for C$_{26}$H$_{22}$FN$_5$OS, 471.55; m/z found 471.9 [M+H]$^+$, $^1$H NMR (400 MHz, DMSO-d$_6$) δ ppm 1.32-1.56 (m, 2H) 1.57-1.72 (m, 1H) 1.73-1.90 (m, 1H) 2.49-2.67 (m, 1H) 3.02-3.22 (m, 1H) 4.09-4.32 (m, 1H) 4.38-4.65 (m, 2H) 6.57-6.79 (m, 1H) 7.18-7.48 (m, 8H) 7.62-7.85 (m, 3H) 7.87-8.07 (m, 1H).

N. Example 15

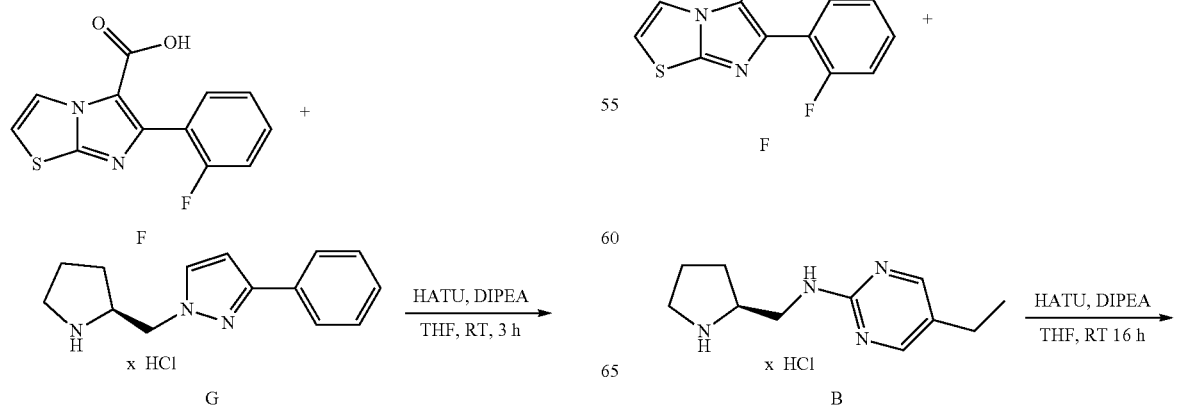

51

-continued

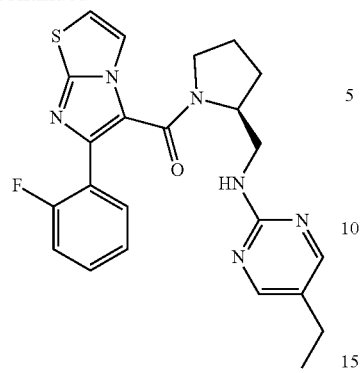

Example 15

Synthesis of Compound Example 15: Compound F (0.026 g, 0.1 mmol) was dissolved in dry THF (2.5 mL). The HATU (0.038 g, 0.1 mmol) was added followed by DIPEA (0.052 g, 0.4 mmol). Compound B (0.024 g, 0.1 mmol) was added to the reaction mixture. The reaction mixture was stirred at ambient temperature for 16 h. LCMS data shows product formation m/z 451. The reaction mixture was diluted with saturated solution of NaHCO$_3$ and extracted with ethyl acetate. The ethyl acetate layer was separated and dried over anhydrous Na$_2$SO$_4$. The evaporation of solvent gave crude product. The crude product was purified by prep-TLC plate, mobile phase: EtOAc:Hexane (75:25 v/v mL). The desired product band was isolated to obtain 0.034 g of product (yield 76.0%). MS (ESI) mass calcd. for C$_{23}$H$_{23}$FN$_6$OS, 450.5; m/z found 450.9 [M+H]$^+$, $^1$H NMR (400 MHz, DMSO-d$_6$) δ ppm 1.01-1.26 (m, 3H) 1.52-1.93 (m, 4H) 2.20-2.43 (m, 2H) 2.55-3.22 (m, 2H) 3.47-3.75 (m, 2H) 3.80-4.50 (br s, 1H) 6.80-6.90 (m, 1H) 7.1-7.28 (m, 3H) 7.32-7.45 (br s, 1H) 7.46-7.65 (m, 2H) 7.67-7.95 (m, 1H) 8.0-8.25 (br s, 1H).

O. Example 16

52

-continued

Example 16

Synthesis of Compound Example 16: Compound M (0.02 g, 0.08 mmol) was dissolved in dry DCM (2.0 mL). The EDC·HCl (0.029 g, 0.15 mmol) and HOBt (0.021 g, 0.15 mmol) were added followed by Et$_3$N (0.11 mL, 0.8 mmol). Compound G (0.017 g, 0.08 mmol) was dissolved in dry DCM (2.0 mL) and added to the reaction mixture. The reaction mixture was stirred at ambient temperature for 16 h. LCMS data shows product formation m/z 473. The reaction mixture was diluted with DCM and washed with saturated solution of NaHCO$_3$. The DCM layer was separated and dried over anhydrous Na$_2$SO$_4$. The evaporation of solvent gave crude product. The crude product was purified by prep-TLC plate, mobile phase: EtOAc:Hexane (50:50 v/v mL). The desired product band was isolated to obtain 0.002 g of product (yield 5.5%). MS (ESI) mass calcd. for C$_{25}$H$_{21}$FN$_6$OS, 472.5; m/z found 473.2 [M+H]$^+$, $^1$H NMR (400 MHz, CHLOROFORM-d) δ ppm 1.39-1.49 (m, 1H) 1.7-1.85 (m, 1H) 1.86-2.10 (m, 1H) 2.11-2.35 (m, 1H) 2.93 (dt, J=10.62, 7.09 Hz, 1H) 3.14 (dt, J=10.66, 6.67 Hz, 1H) 3.81 (br d, J=5.80 Hz, 1H) 4.49-4.73 (m, 2H) 6.55 (d, J=2.27 Hz, 1H) 6.97-7.23 (m, 2H) 7.23-7.29 (m, 2H) 7.32-7.42 (m, 2H) 7.55-7.65 (m, 1H) 7.69-7.82 (m, 3H) 8.63 (s, 1H).

P. Example 17

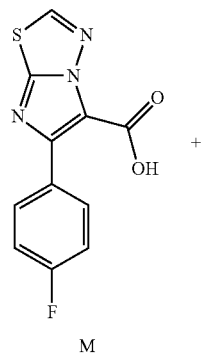

M

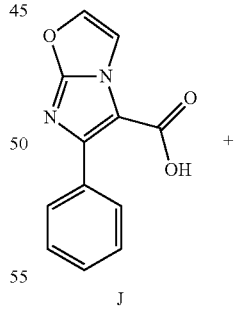

J

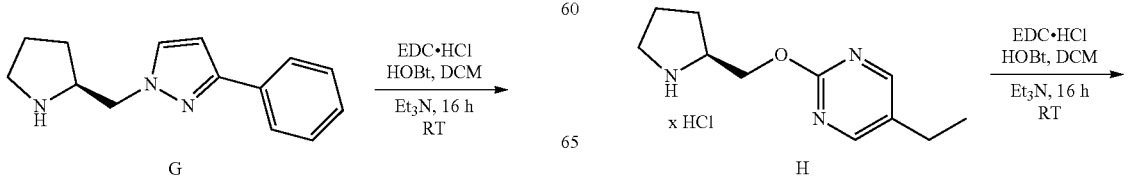

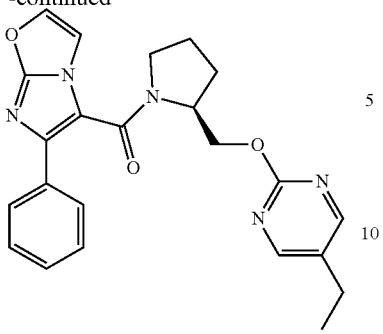

Example 17

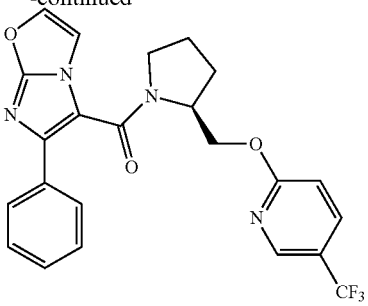

Example 18

Synthesis of Compound Example 17: Compound J (0.025 g, 0.11 mmol) was dissolved in dry DCM (2.0 mL). The EDC·HCl (0.042 g, 0.22 mmol) and HOBt (0.03 g, 0.22 mmol) were added followed by Et$_3$N (0.15 mL, 1.1 mmol). Compound H (0.034 g, 0.11 mmol) was dissolved in dry DCM (2.0 mL) and added to the reaction mixture. The reaction mixture was stirred at ambient temperature for 16 h. LCMS data shows product formation m/z 418.2. The reaction mixture was diluted with DCM and washed with saturated solution of NaHCO$_3$. The DCM layer was separated and dried over anhydrous Na$_2$SO$_4$. The evaporation of solvent gave crude product. The crude product was purified by prep-TLC plate, mobile phase: EtOAc:Hexane (60:40 v/v mL) to obtain 19.5 mg of pure product (yield 42.7%). MS (ESI) mass calcd. for C$_{23}$H$_{23}$N$_5$O$_3$, 417.5; m/z found 418.2 [M+H]$^+$, $^1$H NMR (400 MHz, CHLOROFORM-d) b ppm 1.17-1.24 (t, J=8.0 Hz, 3H) 1.38-1.82 (m, 2H) 1.82-2.23 (m, 2H) 2.45-2.62 (q, J=8.0 Hz, 2H) 2.62-2.89 (m, 1H) 3.11-3.40 (m, 1H) 3.53-4.22 (br, 1H) 4.36-4.86 (m, 2H) 7.26-7.50 (m, 5H) 7.51-7.72 (m, 2H) 8.35 (br s, 2H).

Q. Example 18

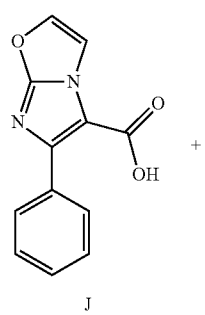

J

+

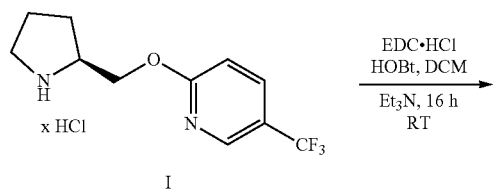

I

→ EDC·HCl HOBt, DCM Et$_3$N, 16 h RT

Synthesis of Compound Example 18: Compound J (0.025 g, 0.11 mmol) was dissolved in dry DCM (2.0 mL). The EDC·HCl (0.042 g, 0.22 mmol) and HOBt (0.03 g, 0.22 mmol) were added followed by Et$_3$N (0.15 mL, 1.1 mmol). Compound I (0.035 g, 0.11 mmol) was added to the reaction mixture. The reaction mixture was stirred at ambient temperature for 16 h. LCMS data shows product formation m/z 457.2. The reaction mixture was diluted with DCM and washed with saturated solution of NaHCO$_3$. The DCM layer was separated and dried over anhydrous Na$_2$SO$_4$. The evaporation of solvent gave crude product. The crude product was purified by prep-TLC plate, mobile phase: EtOAc:Hexane (40:60 v/v mL) to obtain 0.027 g of product (yield 53.0%). MS (ESI) mass calcd. for C$_{23}$H$_{19}$F$_3$N$_4$O$_3$, 456.4; m/z found 457.2 [M+H]$^+$, $^1$H NMR (400 MHz, CHLOROFORM-d) δ ppm 1.42-2.19 (m, 4H) 2.45-2.93 (m, 1H) 3.15-3.45 (m, 1H) 4.22-4.97 (m, 3H) 6.73-6.95 (br, 1H) 7.31 (br s, 3H) 7.36-7.44 (m, 1H) 7.60 (br s, 3H) 7.71-7.84 (m, 1H) 8.27-8.58 (m, 1H).

III. Biological Assays Experimental

Antagonistic activities on both orexin receptors have been measured for each example compound using the following procedure:

In Vitro Assay: Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 µg/mL G418, 100 U/mL penicillin, 100 µg/mL streptomycin and 10% heat inactivated fetal calf serum (FCS). The cells are seeded at 20'000 cells/well into 384-well black clear bottom sterile plates (Greiner). The seeded plates are incubated overnight at 37° C. in 5% CO$_2$. Human orexin-A as an agonist is prepared as 1 mM stock solution in MeOH:water (1:1), diluted in HBSS containing 0.1% bovine serum albumin (BSA), NaHCO$_3$: 0.375 g/L and 20 mM HEPES for use in the assay at a final concentration of 3 nM.

Antagonists are prepared as 10 mM stock solution in DMSO, then diluted in 384-well plates using DMSO followed by a transfer of the dilutions into in HBSS containing 0.1% bovine serum albumin (BSA), NaHCO$_3$: 0.375 g/L and 20 mM HEPES. On the day of the assay, 50 µL of staining buffer (HBSS containing 1% FCS, 20 mM HEPES, NaHCO$_3$: 0.375 g/L, 5 mM probenecid (Sigma) and 3 µM of the fluorescent calcium indicator fluo-4 AM (1 mM stock solution in DMSO, containing 10% pluronic) is added to each well. The 384-well cell-plates are incubated for 50 min at 37° C. in 5% CO$_2$ followed by equilibration at RT for 30 min before measurement.

Within the Fluorescent Imaging Plate Reader (FLIPR Tetra, Molecular Devices), antagonists are added to the plate in a volume of 10 μL/well, incubated for 120 min and finally 10 μL/well of agonist is added. Fluorescence is measured for each well at 1 second intervals, and the height of each fluorescence peak is compared to the height of the fluorescence peak induced by 3 nM orexin-A with vehicle in place of antagonist. The IC50 value (the concentration of compound needed to inhibit 50% of the agonistic response) is determined and may be normalized using the obtained IC50 value of an on-plate reference compound. Optimized conditions were achieved by adjustment of pipetting speed and cell splitting regime. The calculated IC50 values may fluctuate depending on the daily cellular assay performance. Fluctuations of this kind are known to those skilled in the art. In the case where IC50 values have been determined several times for the same compound, the geometric mean has been given. Antagonistic activities of example compounds are shown in Tables 1 and 2.

TABLE 1

Example of Compound data (% Inhibition at Orexin receptor type 1 and type 2, @ 1 uM)

| Example | % Inhibition of $OX_1R$ @1 uM compound | % Inhibition of $OX_2R$ @1 uM compound |
|---|---|---|
| 1 | 70.36 | 26.56 |
| 2 | 83.04 | 39.90 |
| 3 | 45.80 | 14.44 |
| 4 | 61.13 | 25.43 |
| 5 | 0.50 | 3.30 |
| 6 | −5.39 | 16.23 |
| 7 | 48.12 | 6.75 |
| 8 | 81.64 | 1.80 |
| 9 | 81.41 | 10.70 |
| 10 | 63.48 | 9.37 |
| 11 | 16.06 | 12.01 |
| 12 | 79.76 | 11.77 |
| 13 | 62.79 | 29.01 |
| 14 | 87.38 | 57.00 |
| 15 | 25.07 | 15.18 |
| 16 | 90.30 | 34.38 |
| 17 | 4.50 | 8.06 |
| 18 | 37.11 | 14.90 |

TABLE 2

Selected Compound $IC_{50}$ Example at Orexin receptor type 1 and type 2

| Example | IC50 $OX_1R$ (nM) | Kb $OX_1R$ (nM) | IC50 $OX_2R$ (nM) | Kb $OX_2R$ (nM) |
|---|---|---|---|---|
| 8 | 11 | 2 | | |
| 9 | 18 | 4 | | |
| 10 | 270 | 57 | | |
| 12 | 13 | 3 | | |
| 14 | 12 | 3 | 1750 | 241 |
| 16 | 7 | 1.5 | | |

While certain embodiments have been described in terms of the preferred embodiments, it is understood that variations and modifications will occur to those skilled in the art. Therefore, it is intended that the appended claims cover all such equivalent variations that come within the scope of the following claims.

What is claimed is:

1. A compound of formula I:

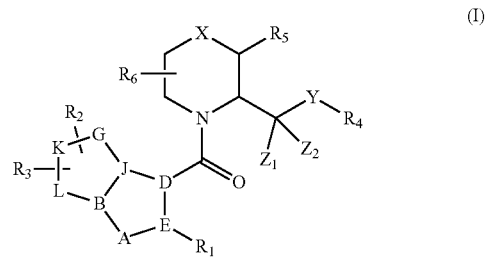

or a pharmaceutically acceptable salt, hydrate, solvate, isomer, or combination thereof, wherein:

$R_1$ is independently is selected from the group consisting of aromatic, aryl, five- or six-member heteroaryl, substituted aromatic, substituted aryl, substituted five- or six-member heteroaryl; optionally wherein the heteroaryl is selected from the group consisting of pyrrolyl, pyrazolyl, triazolyl, oxazolyl, thiazolyl, oxadiazolyl, thiophenyl, pyridinyl, pyrimidinyl, pyrazinyl, and pyridazinyl; wherein said aromatic, aryl or heteroaryl is unsubstituted, mono-substituted by one $R_{1a}$ substituent, or di-substituted by two $R_{1a}$ substituents, wherein each $R_{1a}$ substituent is independently selected from the group consisting of $(C_{1-4})$alkyl, $(C_{1-4})$alkoxy, halogen, $(C_{1-3})$fluoroalkyl, $(C_{1-3})$fluoroalkoxy, and $(C_{3-7})$cycloalkyl; wherein the halogen is optionally selected from the group consisting of F, Cl, Br, and I;

$R_2$ and $R_3$ are independently selected from the group consisting of H, halogen, alkyl, substituted alkyl, $(C_{1-4})$alkyl, $(C_{1-4})$alkoxy, halogen, $(C_{1-3})$fluoroalkyl, $(C_{1-3})$fluoroalkoxy, and $(C_{3-7})$cycloalkyl; wherein each of $R_2$ and $R_3$ is independently and optionally substituted at each substitutable position with up to three $R_2$-$R_3$ substituents, wherein each $R_2$-$R_3$ substituent is independently selected from the group consisting of H, halogen, alkyl, substituted alkyl, $(C_{1-4})$alkyl, $(C_{1-4})$alkoxy, halogen, $(C_{1-3})$fluoroalkyl, $(C_{1-3})$fluoroalkoxy, and $(C_{3-7})$cycloalkyl; wherein the halogen is selected from the group consisting of F, Cl, Br, and I;

$R_4$ is selected from the group consisting of aromatic, aryl, five- or six-member heteroaryl, substituted aromatic, substituted aryl, substituted five- or six-member heteroaryl;

wherein said aromatic, aryl or heteroaryl is unsubstituted, mono-substituted by one $R_{4a}$ substituent, di-substituted by two $R_{4a}$ substituents, or tri-substituted by three $R_{4a}$ substituents, wherein each $R_{4a}$ substituent is independently selected from the group consisting of phenyl, $(C_{1-4})$alkyl, $(C_{1-4})$alkoxy, halogen, $(C_{1-3})$fluoroalkyl, $(C_{1-3})$fluoroalkoxy, $(C_{3-7})$cycloalkyl, and $(C_{3-7})$heterocycloalkyl; wherein the halogen is selected from the group consisting of F, Cl, Br, and I;

$R_5$ is selected from the group consisting of:

H, $(C_{1-4})$alkyl, and substituted alkyl when X is absent to provide a pyrrolidine ring; and, $(C_{1-4})$alkyl and substituted alkyl when X is $CH_2$ to provide a piperidine ring;

wherein:

the carbon atom at position 2 of the of the piperidine ring or the pyrrolidine ring is optionally in absolute (S)-configuration; and the carbon atom at position 2 of the morpholine ring is optionally in absolute (R)-configuration;

57

R$_6$ is selected from the group consisting of H, halogen, alkyl group, and substituted alkyl; wherein the halogen is selected from the group consisting of F, Cl, Br, and I;

R$_5$ and R$_6$ are optionally connected as alkyl group to form a (C$_{1-3}$)alkyl bridge cyclic structure;

X is O to provide a morpholine ring, wherein the carbon atom at position 2 of the morpholine ring is optionally in absolute (R)-configuration;

Y is absent of selected from the group consisting of NH, O, CH$_2$OR$_4$, CH$_2$, and NR$_4$R$_7$ where R$_7$ is H or alkyl; and, Z$_1$ and Z$_2$ are each independently selected from the group consisting of H, F, (C$_{1-4}$)alkyl, (C$_{1-3}$)fluoroalkyl, (C$_{1-3}$)fluoroalkoxy, and (C$_{2-7}$)cycloalkyl;

and wherein:

A-B-J-D-E is a five-member heteroaryl;

B-J-G-K-L is a five-member ring selected from the group consisting of aromatic, aryl, heteroaryl, cycloalkyl, and heterocycloalkyl;

D is C;

E is C;

A is N;

B is C;

J is N;

G is C or N;

K is C; and,

L is O or S.

2. A compound of claim 1 formula (II):

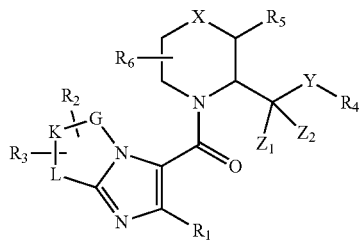

(II)

or a pharmaceutically acceptable salt, hydrate, solvate, isomer, or combination thereof.

3. A compound of claim 1 having formula (III):

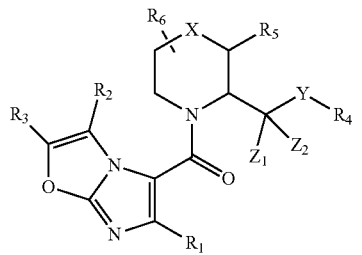

(III)

or a pharmaceutically acceptable salt, hydrate, solvate, isomer, or combination thereof.

58

4. A compound of claim 1 having formula (IV):

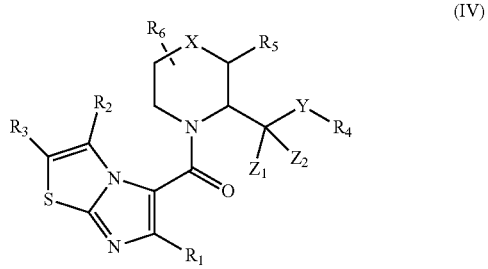

(IV)

or a pharmaceutically acceptable salt, hydrate, solvate, isomer, or combination thereof.

5. A compound of claim 1 having formula (V):

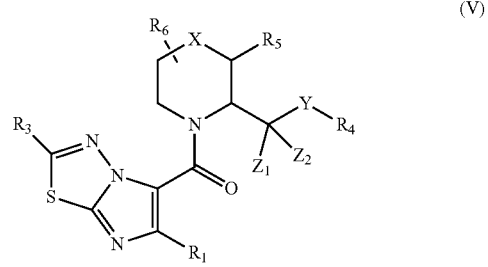

(V)

or a pharmaceutically acceptable salt, hydrate, solvate, isomer, or combination thereof.

6. A compound of claim 1 having formula (VI):

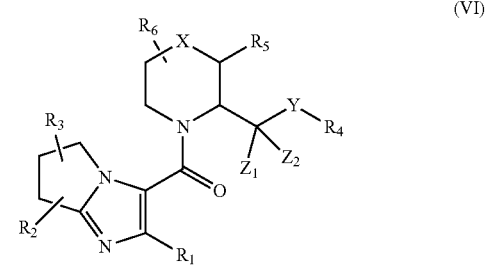

(VI)

or a pharmaceutically acceptable salt, hydrate, solvate, isomer, or combination thereof.

7. A composition comprising a compound, pharmaceutically acceptable salt, hydrate, solvate, isomer, or combination thereof according to claim 1.

8. A pharmaceutical composition comprising a compound, pharmaceutically acceptable salt, hydrate, solvate, isomer, or combination thereof, of claim 1; and at least one pharmaceutically acceptable excipient, carrier, adjuvant, or vehicle.

9. The pharmaceutical composition of claim 8 comprising a therapeutically effective amount of the compound, pharmaceutically acceptable salt, hydrate, solvate, isomer, or combination thereof.

10. The pharmaceutical composition according to claim 8, wherein said composition further comprises at least one second therapeutic agent.

11. A method for treating a central nervous system (CNS) disorder in a subject in need thereof, the method comprising the step of administering to the subject a composition comprising a compound, pharmaceutically acceptable salt, hydrate, solvate, isomer, or combination thereof, of claim 1.

12. The method of claim 11 wherein the composition comprises a therapeutically effective amount of the compound, pharmaceutically acceptable salt, hydrate, solvate, isomer, or combination thereof.

13. The method of claim 11 wherein the composition comprises a pharmaceutically acceptable salt or isotope of the compound.

14. The method of claim 13 wherein the composition comprises an unlabeled form of the compound or an isotopically labeled form of the compound in which the compound has a structure depicted by the formula wherein one or more atoms are replaced by an atom having a selected atomic mass or mass number.

15. The method of claim 11 wherein the CNS disorder is selected from the group consisting of substance addiction, dependence, panic, anxiety, depression, posttraumatic stress disorder (PTSD), neurodegeneration, autism, schizophrenia, and Alzheimer disease (AD).

16. The method of claim 15 wherein the CNS disorder is substance addiction and/or substance dependence.

* * * * *